| United States Patent [19] | [11] | 4,363,817 |
|---|---|---|
| Biddlecom | [45] | Dec. 14, 1982 |

[54] ENOL ACYLATE ANALOGS OF E$_1$ AND E$_2$ PROSTAGLANDINS

[75] Inventor: William G. Biddlecom, Elkhart, Ind.

[73] Assignee: Miles Laboratories, Inc., Elkhart, Ind.

[21] Appl. No.: 296,857

[22] Filed: Aug. 27, 1981

[51] Int. Cl.$^3$ .................. C07C 177/00; A61K 31/557
[52] U.S. Cl. .................................... 424/311; 546/226; 560/106; 560/107; 560/118; 560/121; 560/185; 560/187; 560/193; 560/194; 560/231; 560/252; 560/255; 560/256; 260/410; 560/220; 560/221
[58] Field of Search .............. 560/231, 121, 252, 185, 560/193, 118, 255, 256, 187, 106, 107, 194, 220, 221; 546/226; 424/305, 311, 313; 260/410

[56] References Cited

U.S. PATENT DOCUMENTS 4,159,998  7/1979  Kluender ...................... 560/231

OTHER PUBLICATIONS

Vobe, J. of Chromatography, 214, 177, (1981).
Marino, J. Org. Chem. 46, 4389, (1981).

*Primary Examiner*—Robert Gerstl
*Attorney, Agent, or Firm*—Jerome L. Jeffers

[57] ABSTRACT

Disclosed are C-9 enol acylate analogs of E$_1$ and E$_2$ prostaglandins which are variously useful as bronchodilators, gastric anti-secretory agents and cyto-protective agents.

38 Claims, No Drawings

ENOL ACYLATE ANALOGS OF $E_1$ AND $E_2$ PROSTAGLANDINS

BACKGROUND OF THE INVENTION

The compounds of this invention are enol acylate analogs of $E_1$ and $E_2$ prostaglandin derivatives.

Natural prostaglandins are alicyclic compounds related to prostanoic acid, the structure of which is:

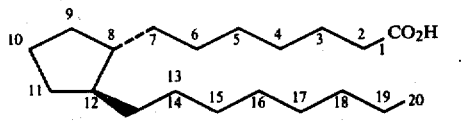

By convention, the carbon atoms of I are numbered sequentially from the carboxylic carbon atom. An important stereochemical feature of (I) is the trans-orientation of the side chains $C_1$-$C_7$ and $C_{13}$-$C_{20}$. In (I), as elsewhere in this specification, solid lines (———) provide a reference plane (such as the cyclopentyl ring or the bonds among $C_1$-$C_7$ and $C_{13}$-$C_{20}$); a dashed line (----) indicates projection of a covalent bond below such reference plane (alpha-configuration); while a wedge line (———) represents projection above such plane (beta-configuration). These conventions apply to all structural formulae subsequently discussed in this specification. In some structures, however, a swung dash or serpentine line ( ∼ ) denotes orientation of a covalent bond either above or below the plane of reference. The compounds of the present invention have a double bond at either the $C_8$-$C_9$ position. When the double bond is at $C_8$-$C_9$, the $C_7$-$C_8$ bond is in the α configuration and the side chains are trans in relation to each other. When the double bond is at $C_9$-$C_{10}$, the $C_7$-$C_8$ bond will be in the reference plane.

Natural prostaglandins have the general structure,

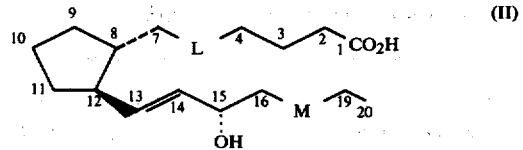

in which L and M may be ethylene or cis-vinylene radicals. Prostaglandins are characterized by the substituents on the cyclopentyl ring, the position of double bonds, if any, in the cyclopentyl ring and the number of double bonds in the side chains. When the cyclopentyl ring is fully saturated, carbonyl substituted at the 9-position and hydroxyl substituted at the 11-position, an E-class prostaglandin (PGE) is represented and when there is a single double bond in the sidechains, i.e., L and M in Formula (II) are ethylene, a type-I prostaglandin is represented. The naturally occurring E-class type 1 prostaglandin known as prostaglandin $E_1$ or $PGE_1$, is represented by the formula:

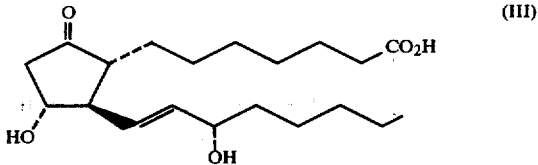

When there is a double bond at $C_5$-$C_6$, i.e., L in Formula (II) is cis-vinylene, prostaglandin $E_2$ or $PGE_2$ is depicted.

Recent research indicates that certain prostaglandins, including $PGE_1$ and $PGE_2$ and derivatives thereof, elicit biochemical and physiological effects in a variety of mammalian systems. For example, in rats, $PGE_1$ increases the release of growth hormone and in sheep it has been found to inhibit ovarian progesterone secretion. In mice, $PGE_1$ has been found to increase thyroid activity whereas in hyphosectomized rats it has been found to stimulate stereordogenisis in the adrenal glands.

In the mammalian male reproductive system, $PGE_1$ contracts the smooth muscle of the vas deferens and in the female reproductive system $PGE_1$ compounds contract uterine smooth muscle. Prostaglandins stimulate contraction of gastrointestinal smooth muscle in vivo and in vitro. In dogs, $PGE_1$ inhibits gastric secretion and, in most mammalian respiratory tracts, PGE compounds affect in vitro preparation of tracheal smooth muscle. The human lung normally contains PGE compounds; consequently some cases of bronchial asthma may involve an imbalance in the production or metabolism of these compounds.

In addition, prostaglandins are involved in certain hematic mechanisms in mammals. For example, $PGE_1$ inhibits aggregation of blood platelets in vitro. In a variety of mammalian cardiovascular systems, PGE compounds are vasodilators by virtue of their action on vascular smooth muscle.

The various therapeutic uses for $PGE_2$ compounds include induction of human labor, parturition, abortion, luteolysis, as human bronchodilators as well as many of those uses mentioned for $PGE_1$ compounds.

Accordingly, it can be seen that prostaglandins and their analogs have broad clinical implications and research in this area continues in laboratories throughout the world.

The present invention involves 9-enol acylate derivatives of $PGE_1$ and $PGE_2$. Acyloxy prostaglandin analogs have been reported in U.S. Pat. Nos. 3,636,120; 3,723,528 and 4,105,792; however, C-9 enol acylated prostaglandin analogs have not been reported in the patent or scientific literature.

Floyd et al disclose in *J.Org.Chem.*, 44,71 (1979) the utilization of the enol acetate (1) as an intermediate in the synthesis of 11-deoxy cyclopentenones (2) which were then transformed to 11-deoxy prostaglandins.

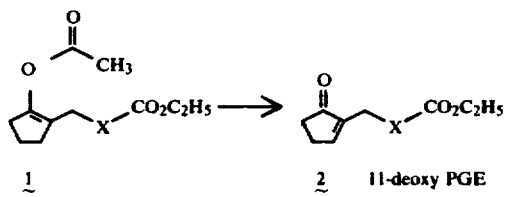

$X = (CH_2)_n$,
$-(CH_2)_3-C(CH_3)_2CH_2-$
$n = 2-4$

Davis et al report in *J.Org.Chem.*, 44, 3755 (1979) the preparation of $PGF_{2\alpha}$ via conjugate addition and regiospecific enolate trapping. Thus the enolate (3) was trapped with various synthons to yield C-8 carbon alkylated prostaglandin intermediates (4). Also stated in this paper was that the enolate (3) "should be effectively trapped with $Me_3SiCl$, acetic anhydride, $ClPO(OEt)_2$, acyl chlorides, aldehydes, and reactive Michael acceptors". The present invention demonstrates the efficient trapping with a few of these reagents at the C-9 oxygen but not at C-8.

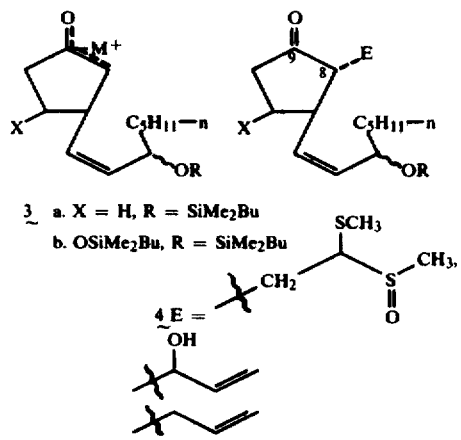

Copending application Ser. No. 154,384 discloses 1-acyloxy-15-deoxy-16-hydroxy prostaglandin $E_1$ analogs characterized by the formula:

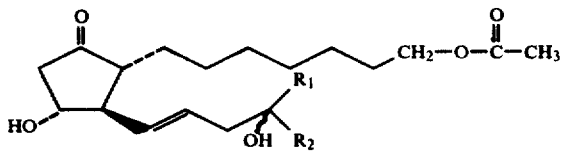

where $R_1$ and $R_2$ are straight or branched chain alkyl groups.

SUMMARY OF THE INVENTION

The present invention involves prostaglandin C-9 enol acylate analogs characterized by the formula:

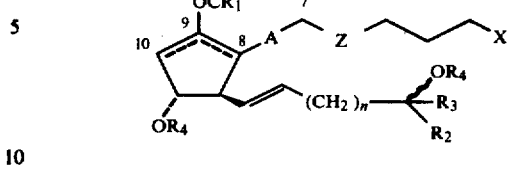

wherein:

the dashed line in the cyclopentyl ring represents the presence of a double carbon-carbon bond at either $C_8-C_9$ or $C_9-C_{10}$; Z is cis vinylene or ethylene; n is 0 or 1; A represents the presence of a single carbon-carbon bond between $C_7$ and $C_8$ which is in the α-configuration when there is a double carbon-carbon bond between $C_7$ and $C_{10}$ and is in a plane of the 5 membered ring when there is a double carbon-carbon bond between $C_8$ and $C_9$; X is $CH_2OH$, $CH_2OCOCH_3$, $CO_2M$ where M is $H^+$, $Na^+$, $K^+$, $\frac{1}{2}Ca^{++}$, $NH^+_3C(C_2H_5OH)$, $CH_3$, $C_2H_5$ or another pharmacologically acceptable salt cation or ester or $CONHR_4$; $R_1$ is n-alkyl of 1 to 20 carbon atoms which is optionally substituted with O, N or S, cyclic alkyl of 3 to 12 carbon atoms optionally substituted with O, N or S, bicyclic alkyl of 7 to 12 carbon atoms, aryl of 6 to 12 carbon atoms optionally substituted with an n-alkyl group of 1 to 10 carbon atoms or one or more halogen atoms, alkenyl (Z and/or E) of 2 to 12 carbon atoms, alkenyl alkyl of 3 to 12 carbon atoms or O-n-alkyl of 1 to 20 carbon atoms wherein all of the above are optionally substituted with $CO_2M$, $CONHR_4$ or acetate; $R_2$ is H, n-alkyl of 1 to 10 carbon atoms, branched alkyl of 3 to 10 carbon atoms, cyclic alkyl of 3 to 10 carbon atoms optionally substituted with n-alkyl of 1 to 10 carbon atoms, bicyclic alkyl of 7 to 12 carbon atoms, aryl of 6 to 12 carbon atoms optionally substituted with n-alkyl of 1 to 10 carbon atoms, halogen, O, N or S; $R_3$ is a moiety coming within the definition of $R_2$ except that $R_3$ is not H; and $R_4$ is H or a moiety coming within the definition of $COR_1$.

DETAILED DESCRIPTION

The presently claimed 9-enol anylate derivatives can be envisioned as prodrugs of the prostaglandin $E_1$ and $E_2$ class. As such they can undergo enzymatic hydrolysis (e.g., with the esterase lipase) to form the respective $E_1$ or $E_2$ prostaglandin analog. Similarly, nonenzymatic hydrolysis of the 9-enol acylates also yields the respective $E_1$ or $E_2$ prostaglandin analog.

The 9-enol acylates can be further modified by interaction of an unprotected hydroxy compound with a carboxyacylating agent preferably a carboxylic acid anhydride. For example, the anhydrides or mixed anhydrides of alkanoic, cycloalkanoic, branched alkanoic, alkenoic, cycloalkenoic, arylalkanoic, aromatic and heterocyclic carboxylic acids can be used as the carboxylating agent. After further processing the prostaglandin analogs of the following formula are produced:

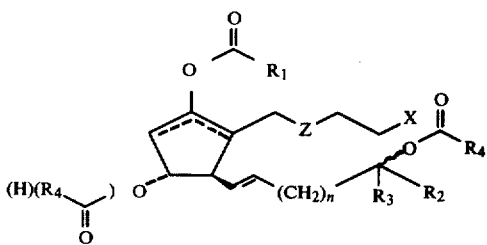

where n, R₁₋₄, Z and X are as previously defined.

The purpose of preparing these pro-drugs is to allow more of the active drug (i.e., as the prostaglandin of the E₁ or E₂ class) to reach the target organ (e.g., the lungs or stomach) so that a longer duration of action is obtained. In prostaglandin drug therapy, compounds of the E class are usually quite active in small amounts (≦10 mg/kg dosages) and of short duration of action. Thus even less of the corresponding pro-drug needs to be administered in order to effect the same (or longer) duration of action. In addition, some prostaglandins of the E class are liable towards elimination of the 11-hydroxy group (under even slightly acidic or basic conditions) to form prostaglandins of the A or B class. This mode of degradation is greatly diminished by the presence of the enol acylate functionality, e.g., enol acetate at C-9. Once hydrolysis of the enol acylate to the C-9 carbonyl occurs, i.e., to the PGE₁ or PGE₂ daughter analog, elimination to the A or B class prostaglandin can then proceed. Under acidic conditions, these enol acylated analogs are quite stable to hydrolysis while their E class prostaglandin counterparts are not. Thus, the pro-drugs of the present invention have a longer shelflife than their respective counterparts of the E class.

The method for the preparation of the compounds is set out in Schemes (I), (II) and (III). Referring to Scheme I, the hydroxy group(s) of 4R-hydroxy-2-[7-hydroxyheptyl]-2-cyclopenten-1-one, or 4R-hydroxy-2-[6-carbomethoxyhexyl]-2-cyclopenten-1-one, or 4R-hydroxy-2-[7-acetoxyheptyl]-2-cyclopenten-1-one (compounds of Formula V) are protected by methods familiar to those skilled in the art (see: "Protective Groups in Organic Chemistry", J. F. W. McOmie (Ed.), Plenum Press, New York (1973)) to provide a compound of structural Formula VI where E is an acid labile hydroxyl protecting group specifically a tetrahydropyran-2-yl or 1-ethoxyethyl or trimethylsilyl (the latter of which can be optionally removed under neutral or basic pH conditions).

The reaction of the appropriate substituted 2-cyclopenten-1-one having the structural Formula VI with the organolithiocuprate of Formula IX, wherein Lig represents a solubilizing ligand. Generally Lig is a tri-(dialkylamino)-phosphine of 6–12 carbon atoms, trialkylphosphine have 3–12 carbon atoms, diarylphosphine, dialkylsulfide having 6–12 carbon atoms. Specifically Lig can be a tri-(dimethylamino)phosphine, tri(n-butyl)phosphine, diphenylphosphine, diisopropylsulfide, dibutylsulfide, dimethylsulfide, diphenylsulfide or di(trimethylsilyl)amino group.

R' is iodide, thiphenylate, alkyn-1-yl having 3 to 8 carbon atoms or R'';

R'' is a radical having the formula:

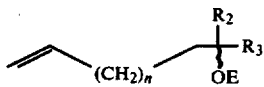

E is an acid-labile hydroxyl-protecting group, specifically a tetrahydropyran-2-yl or 1-ethoxyethyl, or trimethylsilyl.

n=0, 1

R₂, R₃ are as previously defined.

The compounds of the present invention, Formula XII, are prepared via the 1,4 conjugate addition of a 2-cyclopenten-1-one and an organolithiocuprate as reported by Sih et al. (J.Amer.Chem.Soc., 97, 857 and 865 [1975] and references cited therein) followed by quenching of the reaction mixture with a carboxylic acid anhydride, a carboxylic acid mixed anhydride or carboxylic acid chloride of Formula X.

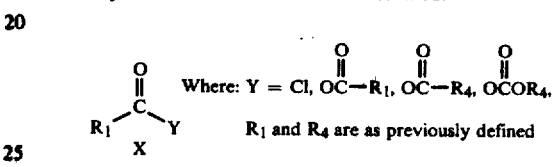

The reaction between compounds of structural Formulae VI and IX in an inert solvent such as ether, tetrahydrofuran, hexane, pentane or toluene, under an inert atmosphere such as nitrogen or argon, at a temperature of from −80° C. to ±10° C., for about 0.25 to three hours, followed by quenching of the reaction mixture with a compound of Formula X at a temperature of from about −80° to +10° C., for about 0.1 to 2.0 hours, provides the intermediate having the structural Formula XI.

Hydrolysis of the intermediate XI provides the prostaglandin XII. Chemical hydrolysis can be accomplished by treatment with a weakly acidic water mixture, e.g., acetic acid-water (65:35 v:v) with 10% tetrahydrofuran, at a temperature of about 20°–45° C. for about 0.5–48 hours. Alternatively chemical hydrolysis of the tetramethylsilyl (TMS) hydroxyl protecting group(s) can be accomplished by treatment with an alcohol-water mixture (typically ethanol-water 2:1 v:v) at a temperature of about 20°–45° C. for about 0.1–4 hours. Compounds of Formula XIII can be accomplished by treatment of the intermediate (Formula XII) with an excess (4 to 100 mole equivalents) of a carboxylic acid anhydride or an acid chloride of the Formula X in the presence of a base such as pyridine for a period of 0.15–14 hours at a temperature of from 0° to 50° C.

All compounds of this invention can be isolated from reaction mixtures and purified by well-known organic chemistry procedures. For example, the compounds can be isolated by dilution of the reaction mixture with water, extraction with a water-immiscible solvent such as benzene, cyclohexane, ether, ethyl acetate, methylene chloride, toluene and the like; chromatography; distillation, crystallization or a combination of these procedures. Purification of these compounds can be accomplished by methods which are well-known in the art for the purification of prostaglandins, lipids, fatty acids, and fatty esters. Such methods as reverse phase partition chromatography; counter-current distribution; adsorption chromatography on acid washed magnesium silicate, neutral or acid washed silica gel, alumina or silicic acid; preparative paper chromatography; preparative thin layer chromatography; high-pressure liquid-liquid chromatography, gas-liquid chromatography; and combinations thereof can be used to purify the compounds produced by the processes of this invention.

Compounds of the type described as Formula XVI (Scheme II) can be prepared by the selective removal of the TMS protecting group of the intermediate XI, as previously described, followed by treatment of the intermediate XIV with an excess amount of a carboxylic acid anhydride or chloride of Formula X in the presence of a base such as pyridine under the conditions previously described (Scheme I). Further processing, as previously described for intermediates XI-XII (Scheme I), produce the prostaglandin analog of Formula XVI.

Alternatively, enol esters of Formula XXI (Scheme III) can be prepared from the known 1-carbinol prostaglandin analogs of Formula XVII such as described in U.S. Pat. Nos. 4,132,738 of Jan. 2, 1979 or 3,636,120 of Jan. 18, 1972, by treatment with hexamethyldisilazane, trimethylsilyl chloride (or other standard silylating reagents as described in the Pierce Handbook and General Catalog, Pierce Chemical Co., Rockford, Ill.) to produce the intermediate described as Formula XVIII. This intermediate is treated with a metallated alkyl amide of Formula XIX, such as lithium diisopropylamide ("*Reagents for Organic Synthesis*" (Vol. 6), L. F. Fieser and M. Fieser, John Wiley & Sons, New York (1977), and references cited therein) in an inert solvent such as tetrahydrofuran, ethyl ether, hexane, dimethoxyethane, dimethylformamide, hexamethylphosphoric triamide, hexamethylphosphorous triamide or mixtures thereof at $-80°$ to $0°$ C., under an inert atmosphere, for 1 minute to 4.0 hours, and the reaction mixture treated with an excess (5 to 100 mole equivalents) of a carboxylic acid anhydride, mixed carboxylic acid anhydride, or carboxylic acid chloride of Formula X, at a temperature of $-80°$ C. to $+20°$ C., for 1 minute to 4.0 hours, followed by an aqueous acid quench, to give an intermediate of Formula XX. This intermediate is treated with an alcohol-water mixture (typically ethanol-water 2:1 v:v) or a mildly acidic mixture (typically acetic acid-water-tetrahydrofuran 2:1:0.1 v:v:v) at 0° C. to 50° C. from 1 minute to 2.0 hours to yield, after standard purification methods, such as previously described, a prostaglandin analogue of Formula XXI.

The preparation of the compounds of this invention is more specifically described in the following examples in which all temperatures are in 0° C. and all solvents are anhydrous and reagent grade unless otherwise specified. In the following examples NMR (pmr and cmr) spectra were determined in CDCl$_3$ and infrared (ir) spectra in CHCl$_3$ unless otherwise noted. Analytical thin layer chromatography was performed on 0.2 mm Silica Gel 60 F 254 plates (EM Reagents) or KC$_{18}$ reverse phase TLC plates (Whatman). "System II" is defined as the organic layer from a mixture of ethyl acetate, acetic acid, isooctane, and water in a ratio of 11:2:5:10. Spots were visualized under uv light and/or by ceric sulfate or Brom-cresol green (for acidic compounds) spray reagents (see K. Schreiber, et al., *J Chromatography*, 12, 63 (1962)). Column chromatographic separations were performed on ICN Silica Gel (32-63 μm partical size) using hexane-ethyl acetate gradient elution unless otherwise specified. Celite ® is a brand name for a diatomaceous earth. High Pressure Chromatography (HPLC) was performed on a Waters, Assoc. Analytical HPLC instrument utilizing one or two Whatman M9 (10/50) partisil normal phase column(s) and isopropanol-hexane mixtures (9.9 ml/min) unless otherwise specified or a Whatman PXS 10/25 reverse phase column and acetonitrile-water mixtures (2 ml/min) as eluant. HPLC peak detection was determined by Waters, Assoc. refractive index (R.I.) and/or ultraviolet (uv) (210 nm) detector(s). Preparative HPLC was performed on a Waters, Assoc. Prep 500A instrument using 1,2 or 4 Waters, Assoc. PrePAK 500/SILICA cartridges and ethyl acetate as eluant (250 ml/min.) unless otherwise specified. Mass spectra were determined by Raltech, Inc., Madison, Wis. or by the Chemistry Department of Miles Laboratories, Inc., Elkhart, Ind.

SCHEME I

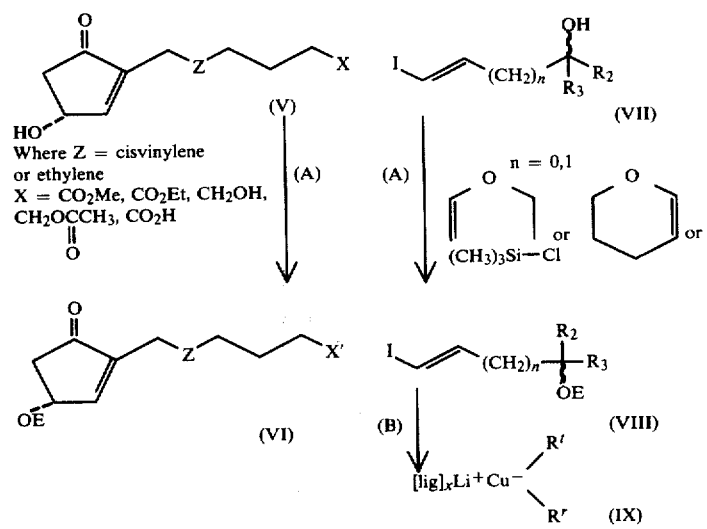

-continued
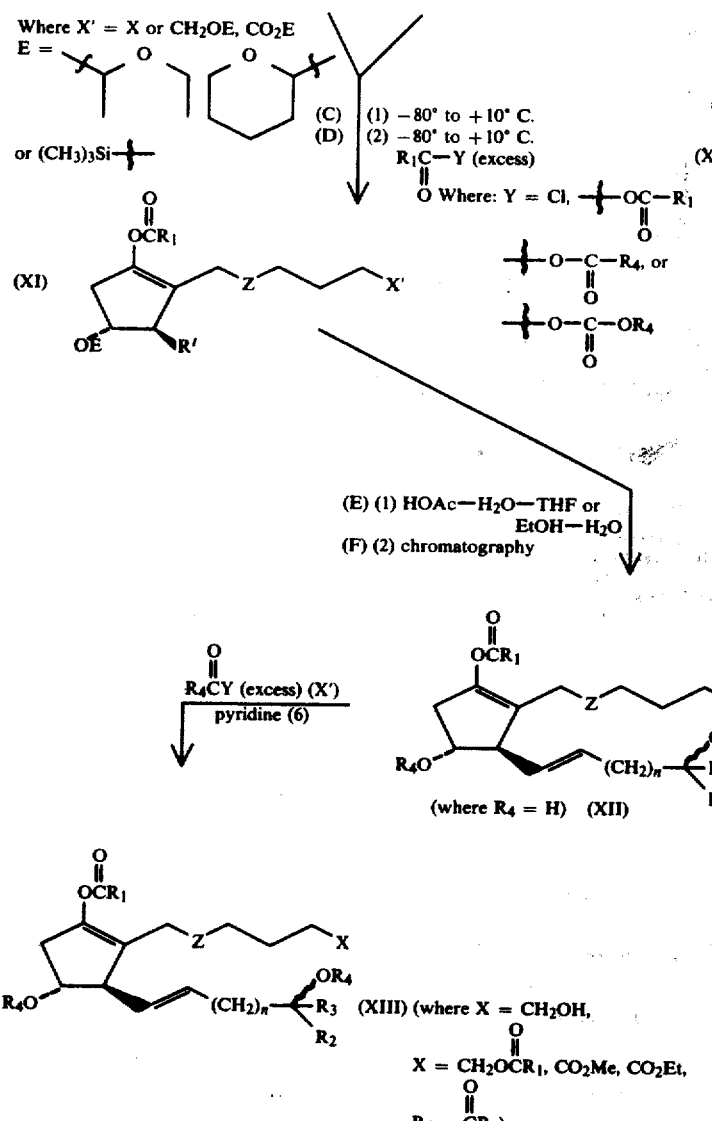
SCHEME II
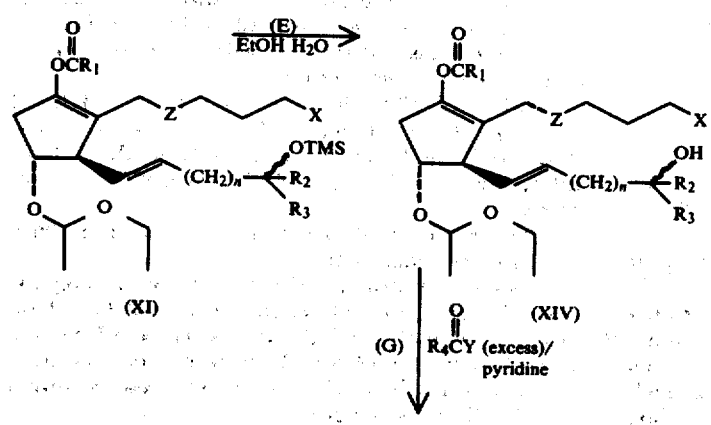

-continued

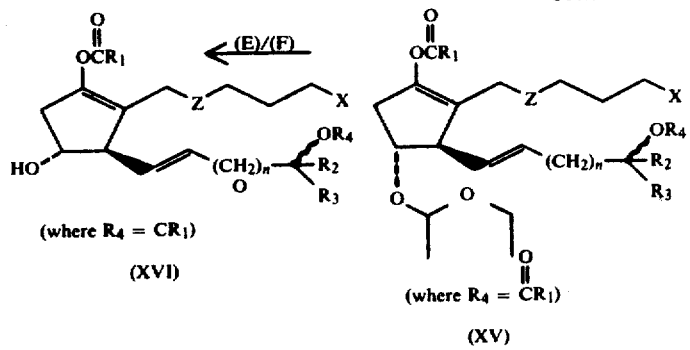

SCHEME III

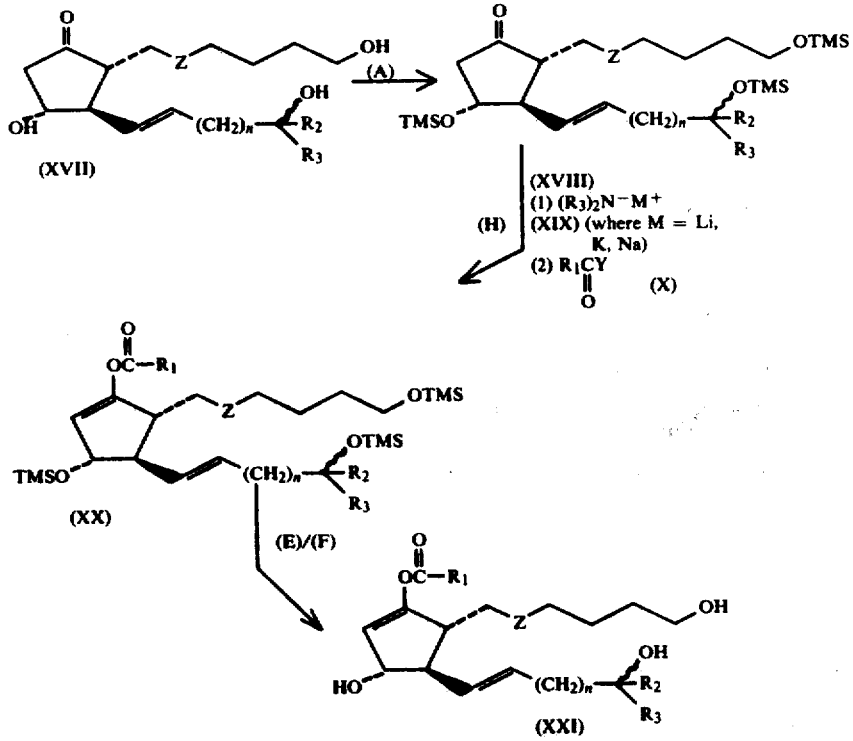

EXAMPLE I

Methyl 9-Acetoxy-11α,15S-Dihydroxyprosta-8,13E-dien-1-oate (TR-7091)

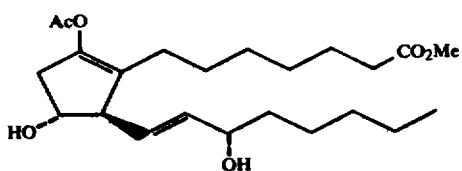

A. Preparation of Organolithiocuprate from Iodovinylalcohol.

(1) Preparation of 1-iodo-3S-trimethylsiloxyoct-1E-ene

To 886 mg. of 1-iodo-3S-hydroxyoct-1E-ene (Sih et al, *J. Amer. Chem. Soc.*, 97, 857 and 865 (1975) and references cited therein) in 4 ml. tetrahydrofuran (THF), under argon, was injected 1.79 ml. hexamethyldisilazane (Aldrich) followed by 94 ml of trimethylsilyl chloride (Aldrich). The reaction mixture was stirred for 14 hours at room temperature, diluted with ether and poured over crushed ice. The ether layer was separated and washed with cold (0° C.) 2% (aq.) sulfuric acid, cold (0° C.) 10% (aq.) sodium bicarbonate and saturated (aq.) brine. The ethereal solution was dried ($Na_2SO_4$) and evaporated in vacuo to yield 909 mg. of the title compound. This material was used in subsequent reactions without further purification.

Analysis: NMR ($CDCl_3$) δ: 0.1 (9H, s), 0.9 (3H, t), 1.2 (8H, m), 3.8–4.2 (1H, m), 6.2 (1H, dd, J=14,8 Hz), 6.65 (1H, dd, J=14,6 Hz); ir ($CHCl_3$): 2950, 2850, 1605, 1445, 1355, 1245, 1160, 1080, 935, 865, 835 $cm^{-1}$; $R_f$ ($CHCl_3$) 0.60.

(2) Preparation of Organolithiocuprate from Protected Iodovinylalcohol

A solution of 816 mg. of 1-iodo-3S-trimethylsilyloxyoct-1E-ene, in 7 ml. of dry ether was stirred in a flask under argon with −78° C. bath cooling as 3.5 ml. of a 1.46 M solution of t-butyllithium in pentane was added dropwise via syringe. The resultant solution was stirred at −78° C. for two hours.

A second solution was prepared by stirring under argon a suspension of 326 mg. of dry copper (I) pentyne in 4 ml. of dry ether solubilized with 0.97 ml. of hexamethylphosphorous triamide, until it becomes homogeneous. This second solution was then transferred via syringe to the above alkenyl lithium reaction mixture as it was stirred with −78° C. bath cooling. The desired lithiocuprate reagent, an orange mixture, was stirred 15 minutes after addition was complete.

B. Substituted 2-Cyclopenten-1-one (1) Preparation of 4R-trimethylsilyoxy-2-(6-carbomethoxyhexyl)-2-cyclopenten-1-one The method described in Example I was used to prepare 4R-trimethylsilyloxy-2-(6-carbomethoxyhexyl)-2-cyclopenten-1-one by replacing the 1-iodo-3S-hydroxyoct-1E-ene with 4R-hydroxy-2-(carbomethoxyhexyl)-2-cyclopenten-1-one (C. J. Sih et al., *J. Amer. Chem. Soc.*, 97, 857 and 865 [1975]). The colorless oil (78%) was used without further purification.

Analysis: NMR (CDCl$_3$) δ: 0.15 (9H, s), 1.2–2.9 (12H, m), 2.85 (2H, dd, J=19,6 Hz), 3.7 (3H, s), 5.0 (1H, m), 7.2 (1H, m); ir (CHCl$_3$): 2950, 2850, 1720, 1710, 1640, 1435, 1250, 1065, 960, 900, 835 cm$^{-1}$; ms (E.I.) 312 (p$^+$), 297 (p$^+$—CH$_3$), 281 (p$^+$—OMe), 284 (p$^+$—CO), 75 (base peak); [α]$_D$ +10.8° (c 1.05, CHCl$_3$); R$_f$ (7:3 (v/v) CHCl$_3$-acetone) 0.57.

C. Prostaglandin Synthesis

The synthesis of the prostaglandin analog was achieved as described below.

A solution of 420 mg. of 4R-trimethylsilyloxy-2-(6-carbomethoxyhexyl)-2-cyclopenten-1-one, in 2 ml. of dry ether was added dropwise to the lithiocuprate reaction mixture as stirring was continued at −78° C. After addition was complete, the resultant orange mixture was stirred for 15 minutes at −78° C. and then at −20° C. for 2.0 hours.

The reaction mixture was quenched at −20° with 1.2 ml. dry acetic anhydride and stirred at −20, for 5 minutes. The reaction mixture was diluted with ether (20 ml.) and sufficient 2% aqueous sulfuric acid to give an acidic aqueous phase after stirring. The resultant mixture was thoroughly shaken and then filtered through Celite®. The filter pad was rinsed thoroughly with ether. The filtrate phases were separated and the organic phase was washed with saturated aqueous sodium bicarbonate and brine. It was then dried over MgSO$_4$ and evaporated in vacuo to yield 891 mg. of a yellow oil.

This residue was dissolved in 10 ml. ethanol and 5 ml. water. The mixture was stirred at 35°–40° for 0.5 hour. The mixture was reduced in volume (rotoevaporator) and diluted with a ether-water mixture. The ethereal layer was separated, washed with saturated aqueous brine and dried (MgSO$_4$). The filtrate was evaporated in vacuo to yield 455 mg. of a yellow oil. This residue was chromatographed on 70 ml. of silica gel using 7:3 (v/v) hexaneethyl acetate as eluent to yield 257 mg. (46%) of the PGE$_1$ analog (TR-7091).

Analysis of TR-7091: pmr (CDCl$_3$) δ: 0.9 (3H, bt, J=5 Hz), 1.1–3.2 (23H, m), 2.15 (3H, s), 3.4 (2H, bs), 3.7 (3H, s), 4.15 (2H, m), 5.6 (2H, m); cmr (CDCl$_3$) δ: 174.2 (C-1), 168.7 (C-9a), 142.0 (C-9), 135.9 (C-14), 131.0 (C-13), 126.5 (C-8), 75.0 (C-15), 72.9 (C-11), 56.6 (C-12), 51.4 (C-10); ir (CHCl$_3$): 3600 (s), 3550–3200 (b), 3000, 2940, 2855, 1740, 1440, 1370, 1220, 970 cm$^{-1}$; ms (70 eV) 392 (p-H$_2$O), 350 (p-HOAc), 332 (350-H$_2$O), 318 (p—MeOH-HOAc), 300 (318-H$_2$O), 43 (base peak) (Ac); [α]$_D$ −63.9° (c 1.43, CHCl$_3$); R$_f$(system II) 0.45; u.v. (ethanol) end absorption at 212 nm (5190), 271 nm (205).

EXAMPLE II

9-Acetoxy-1,11α, 15S-Trihydroxyprosta-8,13E-diene (TR-7099)

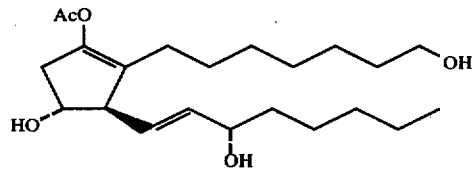

A. Substituted 2-cyclopenten-1-one

Preparation of 4R-Trimethylsilyloxy-2-(7-Trimethylsilyloxyheptyl)-2-Cyclopenten-1-one The method described in Example I was used to prepare 4R-trimethylsilyloxy-2-(7-trimethylsilyloxyheptyl)-2-cyclopenten-1-one by replacing the 1-iodo-3S-hydroxyoct-1E-ene with 4R-hydroxy-2-(7-hydroxyheptyl)-2-cyclopenten-1-one (H. C. Kluender et al, *Tetrahedron Letters*, 2063 [1977]). The pale yellow oil (95%) was used without further purification.

Analysis: nmr (CDCl$_3$) δ: 0.1 (9H, s), 1.2–2.9 (14H, m), 3.6 (2H, t, J=6 Hz), 4.9 (1H, m), 7.1, (1H, m); ir (CHCl$_3$) 3000, 2930, 2855, 1705, 1635, 1350, 1250, 1070, 900, 835 cm$^{-1}$; R$_f$[7:3 (v/v) CHCl$_3$-acetone]0.68.

B. The method described in Example I was used to prepare TR-7099 replacing the 4R-trimethylsilyloxy-6(carbomethoxyhexyl)-2-cyclopenten-1-one with 4R-trimethylsilyloxy-2-(7-trimethylsilyloxyheptyl)-2-cyclopenten-1-one.

The resulting PGE$_1$ analog had the following physical characteristics: m.p. 69°–70°; [α]$_D$ −70.7° (c 1.06,CHCl$_3$); R$_f$ (system II) 0.44; u.v. (ethanol) end absorption at 211 nm (7965); pmr (CDCl$_3$) δ: 0.9 (3H, bt, J=5 Hz), 1.1–3.25 (26H, m), 2.2 (3H, s), 3.65 (2H, t, J=7 Hz), 4.2 (2H, m), 5.6 (2H, m); cmr (CD$_3$)$_2$CO δ: 169.0 (C-9a), 143.4 (C-9), 137.3 (C-14), 131.1 (C-13), 127.2 (C-8), 75.6 (C-15), 72.9 (C-11), 62.7 (C-1), 57.6 (C-12); ir (CHCl$_3$) 3700–3200 (b), 3600 (s), 2930, 2855, 1740, 1595, 1370, 1220, 1050, 970 cm$^{-1}$; ms (70 eV) no parent (382), 365 (p-OH), 364 (p-H$_2$O), 347 (p-OH-H$_2$O), 346 (p-2H$_2$O), 322 (p-HOAc), 304 (322-H$_2$O), 43 (base peak) (Ac).

EXAMPLE III

Ethyl 9-Acetoxy-11α, 15S-Dihydroxyprosta-5Z 8,13E-triene-1-oate (TR-7101)

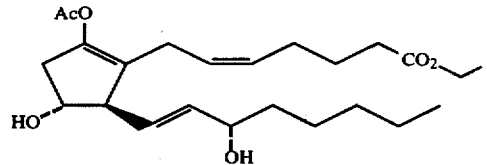

A. Substituted 2-Cyclopenten-1-One

4R-Trimethylsilyloxy-2-(6-carboethoxy-2Z-hexenyl)-2-cyclopenten-1-one was prepared from the appropriate 2-(ω-carboethoxyalkyl)-cyclopenten-1,3,4- trione as described in Sih et al., *J. Amer. Chem. Soc.*, 97, 857 and 865 (1975) and as described in detail herein previously (See Example I).

Analysis: nmr (CDCl₃) δ: 0.2 (9H, s), 1.3 (3H, t, J=7 Hz), 2.6–3.1 (10H, m), 4.2 (2H, q, J=7 Hz), 5.0 (1H, m), 5.6 (2H, d, 5, J=10, 6 Hz), 7.2 (1H, m); ir (CHCl₃)2955, 1715, 1640, 1355, 1250, 1080, 965, 895, 840 cm⁻¹; R$_f$[8:2 (v/v) chloroform-acetone]0.64.

B. The method described in Example I was used to prepare the PGE₂ analog TR-7101 by replacing the 4R-trimethylsilyloxy-2-(6-carbomethoxyhexyl)-2-cyclopenten-1-one with 4R-trimethylsilyloxy-2-(6-carboethoxy-2Z-hexenyl)-2-cyclopenten-1-one. TR-7101 had the following physical characteristics:

TR-7101: [α]$_D$ −91.6° (c 1.0, CHCl₃); R$_f$(system II) 0.37; nmr (CDCl₃) δ: 0.9 (3H, bt, J=6 Hz), 1.25 (3H, t, J=7 Hz), 1.2–3.3 (20H, m), 2.2 (3H, s), 4.2 (4H, bq, J=7 Hz), 5.6 (4H, m); ir (CHCl₃) 3600–3200 (b), 2925, 2855, 1720, 1370, 1180, 965 cm⁻¹; ms (70 eV) no parent, 405 (p-OH), 404 (p-H₂O), 386 (p-2H₂O), 362 (p-HOAc), 344 (362-H₂O), 318 (p-EtO-OAc), 43 (base peak) (Ac).

EXAMPLE IV

9-Acetoxy-16,20-Methano-1,11α,15R-Trihydroxyprosta-8,13E-Diene (TR-7106)

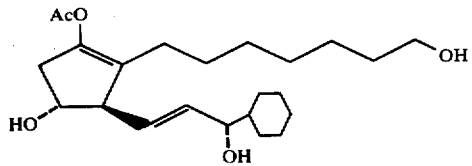

A. Preparation of Organolithiocuprate from Iodovinylalcohol (1) Preparation of 1-Iodo-3R-trimethylsilyloxy -3-Cyclohexyl-1Z-Propene The method described in Example IA was used to prepare 1-iodo-3R-trimethylsilyloxy-3-cyclohexyl-1E propene by replacing the 1-iodo-3S-hydroxyoct-1E-ene with 1-iodo-3R-hydroxy-3-cyclohexyl-1E-propene (H. C. Kluender et al, *Prostaglandins*, 16, 67 [1978]). The resultant yellow oil was used without further purification.

Analysis: nmr (CDCl₃) δ: 0.1 (9H, s), 0.9–2.0 (11H, m), 3.8 (1H, dd, J=6, 5 Hz), 6.2 (1H, d, J=15 Hz), 6.65 (1H, dd, J=15, 6 Hz); ir (CHCl₃) 2925, 2845, 1605, 1475, 1245, 930, 890, 860, 835 cm⁻¹; R$_f$ [9:1 (v/v) hexane-ethyl acetate]0.62.

(2) Preparation of Organolithiocuprate from Protected Iodovinylalcohol

The method described in Example I was used by replacing 1-iodo-3Z-trimethylsilyoxyoct-1E-ene with 1-iodo-3R-trimethylsilyloxy-3-cyclohexyl-1E-propene.

B. The method described in Example II was used to prepare TR-7106 by replacing the 1-iodo-3S-trimethylsilyloxyoct-1E-ene with 1-iodo-3R-trimethylsilyloxy-3-cyclohexyl-1E-propene.

The resulting prostaglandin PGE₁ analog had the following physical characteristics: [α]$_D$−49.9° (c 1.0, CHCl₃); R$_f$(system II) 0.31; m.p. 84°–86°; nmr (CDCl₃) δ: 1.0–3.3 (29H, m), 2.2 (3H, s), 3.65 (2H, bt), 4.15 (2H, m), 5.6 (2H, m); ir (CHCl₃) 3650-3100 (b), 3600 (s), 3000, 2935, 2855, 1740, 1690, 1450, 1365, 1230, 1050, 965, 880 cm⁻¹; ms (70 eV) no parent 376 (p-H₂O), 358 (p-2H₂O), 334 (p-HOAc), 316 (334-H₂O), 43 (base peak) (Ac).

EXAMPLE V

Methyl 9-Acetoxy-16RS-Methyl-11α,15R-Dihydroxy prosta-8,13E-Dien-1-Oate (TR-7110) and Methyl-9-Acetoxy-16RS-Methyl-11α,15S-Dihydroxy-prosta-8,13E-Dien-1-Oate (TR-7111)

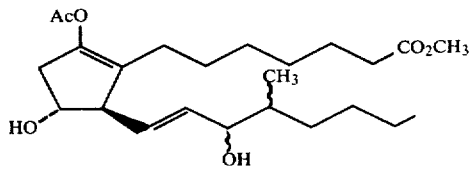

A. Preparation of Organolithiocuprate from Iodovinylalcohol (1) Preparation of 1-Iodo-3-trimethylsilyloxy-4-methyloct-1E-ene The method described in Example I was used to prepare 1-iodo-3-trimethylsilyloxy-4-methyloct-1E-ene by replacing the 1-iodo-3S-hydroxyoct-1E-ene with 1-iodo-3-hydroxy-4-methyloct-1E-ene (Wisconsin Alumni Research Foundation, U.S. Pat. No. 3,962,352 of June 8, 1976). The resultant yellow oil (85%) was used without further purification.

Analysis: nmr (CDCl₃) δ: 0.1 (9H, s), 0.9 (6H, m), 1.3 (7H, m), 4.0 (H, dd, J=6,4 Hz), 6.25 (1H, d, J=14 Hz), 6.65 (1H, dd, J=14,6 Hz); ir (CHCl₃) 2950 2925, 2860, 1605, 1460, 1245, 1070, 940, 920, 870, 835 cm⁻¹; R$_f$[9:1 (v/v) hexane-ethyl acetate] 0.56.

(2) Preparation of Organolithiocuprate from Protected Iodovinylalcohol

The method described in Example I was used by replacing 1-iodo-3S-trimethylsilyloxyoct-1E-ene with 1-iodo-3-trimethylsilyloxy-4-methyloct-1E-ene.

B. The method described in Example I was used to prepare TR-7110 and TR-7111. The resulting prostaglandin PGE₁ analogs had the following spectral characteristics:

TR-7110: [α]$_D$ −54.0° (c 1.0, CHCl₃); R$_f$(system II) 0.44; nmr (CDCl₃) δ: 0.9 (6H, bt), 1.1–3.3 (22H, m), 2.2 (3H, s), 3.75 (3H, s), 4.15 (4H, m), 5.65 (2H, m); ir (CHCl₃) 3700-3200 (b), 3600 (s), 2925, 2850, 1735, 1695, 1365, 1220, 1175, 965 cm⁻¹; ms (70 eV) no parent, 407 (p-OH), 406 (p-H₂O), 388 (p-2H₂O), 365 (p-OAc), 364 (p-HOAc), 346 (364-H₂O), 43 (base peak) (Ac). TR-7111: [α]$_D$ −75.5° (c 1.0, CHCl₃); R$_f$(system II) 0.47; nmr, ir and ms spectra nearly identical to TR-7110.

EXAMPLE VI

Methyl 9-Acetoxy-16,16-Dimethyl-11α,15S-dihydroxyprosta-8,13E-Dien-1-Oate (TR-7112) and Methyl 9-Acetoxy-16,16-Dimethyl-11α,15R-Dihydroxyprosta-8,13E-Dien-1-Oate (TR-7113)

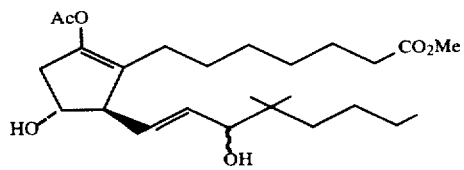

A. Preparation of Organolithiocuprate from Iodovinylalcohol (1) Preparation of 1-Iodo-3-trimethylsilyloxy-4,4-dimethyloct-1E-ene The method described in Example I was used to prepare 1-iodo-3-trimethylsilyloxy-4,4-dimethyloct-1E-ene by replacing the 1-iodo-3S-hydroxyoct-1E-ene with 1-iodo-3-hydroxy-4,4-dimethyloct-1E-ene (Wisconsin Alumni Research Foundation, U.S. Pat. No. 3,962,352 of June 8, 1976). The resultant yellow oil (86%) was used without further purification.

Analysis: nmr (CDCl$_3$) δ: 0.1 (9H, s), 0.9 (9H, bs), 1.2 (6H, m), 3.85 (1H, d, J=6 Hz), 6.25 (1H, d, J=14 Hz), 6.75 (1H, dd, J=15,6 Hz); ir (CDCl$_3$) 2950, 2855, 1600, 1460, 1380, 1360, 1245, 1025, 945, 850, 815 cm$^{-1}$; r$_f$[9:1 (v/v) hexane-ethyl acetate] 0.61.

(2) Preparation of Organolithiocuprate from Protected Iodovinylalcohol

The method described in Example I was used by replacing 1-iodo-3S-trimethylsilyloxyoct-1E-ene with 1-iodo-3-trimethylsilyloxy-4,4-dimethyloct-1E-ene.

B. The method described in Example I was used to prepare TR-7112 and TR-7113. The resulting prostaglandin PGE$_1$ analogs had the following physical characteristics:

TR-7112: [α]$_D$ −63.8° (c 1.0, CHCl$_3$); R$_f$(system II) 0.48; nmr (CDCl$_3$) δ: 0.85 (9H, m), 1.1–3.3 (21H, m), 2.2 (3H, s), 3.75 (3H, s), 3.8 (2H, m), 4.15 (2H, m), 5.65 (2H, m); ir (CHCl$_3$) 3700-3300 (b), 3625 (s) 2940, 2860, 1730, 1440, 1370, 1225, 1180, 970 cm$^{-1}$; ms (70 eV) no parent, 420 (p-H$_2$O), 379 (p-OAc), 360 (378-H$_2$O), 279 (347-(CH$_3$)$_2$CC$_4$H$_9$), 43 (base peak) (Ac). TR-7113: [α]$_D$ −38.6, (c 1.0, CHCl$_3$); R$_f$(system II) 0.44; nmr, ir, and ms nearly identical to TR-7112.

EXAMPLE VI

Ethyl 9-Acetoxy-11α,15S-Dihydroxy-16,16-Dimethylprosta-5Z,8,13E-Triene-1-Oate (TR-7114) and Ethyl 9-Acetoxy-11α,15R-Dihydroxy-16,16-Dimethylprosta-8Z,8,13E-Triene-1-Oate (TR-7115)

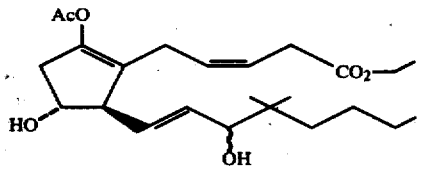

The method described in Example III was used to prepare the prostaglandin PGE$_2$ analogs TR-7114 and TR-7115 by replacing 1-iodo-3S-trimethylsilyloxyoct-1E-3n3 with 1-iodo-3-trimethylsilyloxy-4,4-dimethyloct-1E-ene. The resultant PGE$_2$ analogs had the following spectral characteristics:

TR-7114: [α]$_D$ −83.4° (c 1.0, CHCl$_3$); R$_f$(system II) 0.52; nmr (CDCl$_3$) δ: 0.85 (9H, m), 1.25 (3H, t, J=7 Hz), 1.2–3.3 (17H, m), 2.2 (3H, s), 3.9 (2H, m), 4.2 (4H, bq, J=7 Hz), 5.6 (4H, m); ir (CHCl$_3$) 3700-3250 (b), 3600 (s), 2955, 2870, 1725, 1370, 1225, 1190, 1030, 970 cm$^{-1}$; ms (70 eV) no parent, 432 (p-H$_2$O), 414 (p-2H$_2$O), 407 (p-Ac), 391 (p-OAc), 390 (p-HOAc), 373 (391-H$_2$O), 372 (390-H$_2$O), 372 (390-H$_2$O), 291 (p-HOAc-(CH$_3$)$_2$CC$_4$H$_9$), 245 (291-EtOH), 43 (base peak) (Ac). TR-7115: [α]$_D$ −59.3° (c 1.0, CHCl$_3$); R$_f$(system II) 0.47; nmr, ir and ms nearly identical to TR-7114.

EXAMPLE VIII

Methyl 9-Acetoxy-16,18-Methano-11α,15S-Dihydroxyprosta-8,13E-Dien-1-Oate (TR-7128) and Methyl 9-Acetoxy-16,18-Methano-11α,15R-Dihydroxyprosta-8,13E-Dien-1-Oate (TR-7129)

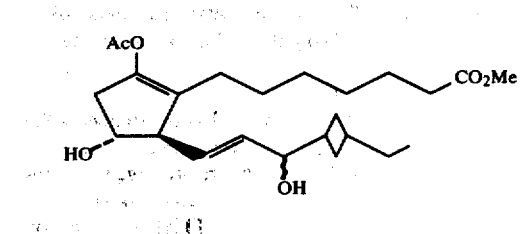

A. Preparation of Organolithiocuprate from Iodovinylalcohol (1) Preparation of 1-iodo-3-trimethylsilyloxy-3-(3-ethylcyclobutyl)-1E-propene.

The method described in Example I was used to prepare 1-iodo-3-trimethylsilyloxy-3-(3-ethylcyclobutyl)-1E-propene by replacing the 1-iodo-3S-hydroxyoct-1E-ene with 1-iodo-3-hydroxy-3-(3-ethylcyclobutyl)-1E-propene (H. C. Kluender et al, Prostaglandins, 16, 67 [1978]). The resultant yellow oil (76%) was used without further purification; R$_f$ [96:4 (v/v) hexaneethyl acetate] 0.55.

(2) Preparation of Organolithiocuprate from Protected Iodovinylalcohol

The method described in Example I was used by replacing 1-iodo-3S-trimethylsilyloxyoct-1E-ene with 1-iodo-3-trimethylsilyloxy-3-(3-ethylcyclobutyl)-1E-propene.

B. The method described in Example I was used to prepare the prostaglandin PGE$_1$ analogs TR-7128 and TR-7129 by replacing 1-iodo-3S-trimethylsilyloxyoct-1E-ene with 1-iodo-3-trimethylsilyloxy-3-(3-ethylcyclobutyl)-1E-propene. The resultant PGE$_1$ analogs had the following spectral characteristics:

TR-7128: [α]$_D$ −71.1° (c 1.12, CHCl$_3$); R$_f$(system II) 0.48; nmr (CDCl$_3$) δ: 0.85 (3H, bt,J=7 Hz), 1.1–3.3 (25H, m), 2.1 (3H, s), 3.75 (3H, s), 4.1 (2H, m), 5.65 (2H, m); ir (CHCl$_3$) 3650-3200 (b), 3600 (s), 2940, 2855, 1735, 1480, 1435, 1370, 1230, 970 cm$^{-1}$; ms (70 eV) no parent, 404 (p-H$_2$O), 363 (p-OAc), 362 (p-HOAc), 345 (363-H$_2$O), 344 (362-H$_2$O), 313 (p-H$_2$O—MeOH—OAc), 312 (p-H$_2$O—MeOH—HOAc), 262 (p-C$_6$H$_{11}$—OAc—H$_2$O), 43 (base peak) (Ac). TR-7129: [α]$_D$ −64.3° (c 1.12, CHCl$_3$); R$_f$(system II) 0.42; nmr, ir and ms nearly identical to TR-7128.

EXAMPLE IX

9-Isobutyloxy-16,20-Ethano-1,11α,15R-Trihydroxyprosta-8,13E-Diene (TR-7131)

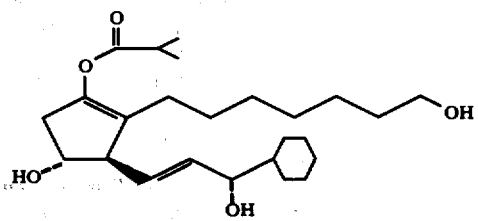

A. Preparation of Organolithiocuprate from Iodovinylalcohol

The method described in H. C. Kluender et al, *Tetrahedron Letters*, 2063 (1977) was followed using 1-iodo-3R-(1-ethoxyethyl)-3-cyclohexyl-1E-propene.

B. Substituted 2-Cyclopenten-1-One

The method described in H. C. Kluender et al, *Tetrahedron Letters*, 2063 (1977) was followed to obtain 4R-(1-ethoxyethyl)-2-[7-(1-ethoxyethyl)-heptyl]-2-cyclopenten-1-one.

C. Prostaglandin Synthesis

The method described in Example I was utilized with the exception that dry isobutyryl chloride was substituted for acetic anhydride and the protecting groups were removed by treatment of the reaction mixture with 65:35:0.1 (v/v) acetic acid-water-THF at 35° for 40 min. After the usual workup and column chromatography purification steps, 144 mg. of the prostaglandin PGE$_1$ analog was obtained. This compound was further purified via HPLC using ethyl acetate (containing 1% methanol) as eluent to obtain TR-7131 as a pale green oil having the following spectral characteristics: [α]$_D$ −45.8° (c 1.0, CHCl$_3$); R$_f$(system II) 0.29; pmr (CDCl$_3$) δ: 1.2 (6H, d, J=7 Hz), 0.9-3.1 (29H, m), 3.6 (2H, 5, J=7 Hz), 3.8 (1H, bt, J=7 Hz), 4.1 (2H, m), 5.5 (2H, bt, J=14, 13 Hz); cmr (CDCl$_3$) δ: 174.9 (C-9a), 142.2 (C-9), 134.2 (C-14), 131.6 (C-13), 126.5 (C-8), 77.4 (C-15), 75.2 (C-11), 63.0 (C-1), 56.9 (C-12); ir (CHCl$_3$) 3650-3100 (b), 3600 (s), 2930, 1740, 1690, 1470, 1450, 1385, 1350, 1255, 1180, 1090, 965, 885 cm$^{-1}$; ms (70 eV) no parent, 404 (p-H$_2$O), 386 (p-2H$_2$O), 316 (p-OCCH(CH$_3$)$_2$-H$_2$O-OH), 290 (p-O$_2$CCH(CH$_3$)$_2$-(CH$_2$)$_2$OH), 43 (base peak) ((CH$_3$)$_2$CH); ms C.I., isobutylene 423 (p+1), 405 (p+1-H$_2$O), 387 (base peak) p+1-2H$_2$O).

EXAMPLE X

9-Acetoxy-1,11α,15R-Trihydroxyprosta-8,13E-Diene (TR-7140)

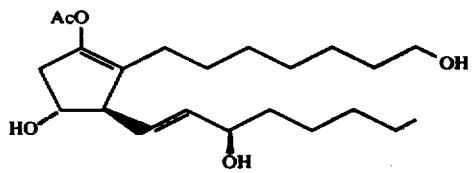

A. Preparation of Organolithiocuprate from Iodovinylalcohol (1) Preparation of 1-Iodo-3R-Trimethylsilyloxyoct-1E-ene.

The method described in Example I was used to prepare 1-iodo-3R-trimethylsilyloxyoct-1E-ene by replacing the 1-iodo-3S-hydroxyoct-1E-ene with 1-iodo-3R-hydroxyoct-1E-ene. The compound 1-iodo-3R-hydroxyoct-1E-ene ([α]$_D$ −10.0° [c 1.0, CH$_3$OH]) was prepared in accordance with Kluge et al, *J. Amer. Chem. Soc.*, 94, 7827 (1972), utilizing (+)-α-methylbenzylamine in lieu of (−)-α-methylbenzylamine. The resultant yellow oil (100%; R$_f$ (CHCl$_3$) 0.61) was used without further purification.

(2) Preparation of Organolithiocuprate from Protected Iodovinylalcohol

The method described in Example I was used by replacing 1-iodo-3S-trimethylsilyloxyoct-1E-ene with 1-iodo-3E-trimethylsilyloxyoct-1E-ene.

B. The method described in Example I was used to prepare TR-7140 utilizing the substituted 2-cyclopenten-1-one described in Example IX.

The resulting prostaglandin PGE$_1$ analog had the following physical characteristics: TR-7140: [α]$_D$ −121.2° (c 1.0, CHCl$_3$); R$_f$ (system II) 0.41; cmr (CDCl$_3$) δ: 168.9 (C-9a), 142.0 (C-9), 135.6 (C-14), 129.9 (C-13), 127.0 (C-8), 75.0 (C-11), 72.2 (C-15), 62.7 (C-1), 56.5 (C-12); pmr, ms and ir nearly identical to TR-7099.

EXAMPLE XI

9-Acetoxy-1,11α,16RS-Trihydroxy-16-Methylprosta-8,13E-Diene (TR-7141) and
9-Acetoxy-1,11α,16RS-Trihydroxy-16-Methylprosta-8,13Z-Diene (TR-7142)

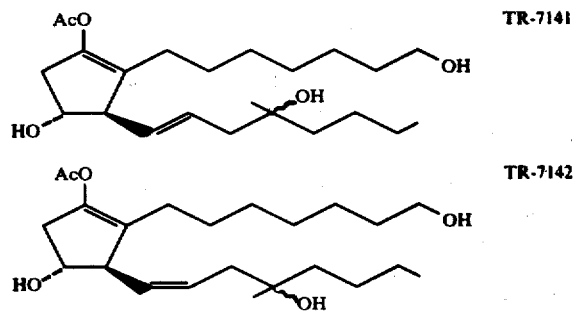

A. Preparation of Organolithiocuprate from Iodovinylalcohol (1) Preparation of 1-Iodo-4RS-(2-Ethoxyethoxy)-4-Methyloct-1E-ene and 1-Iodo-4RS-(2-Ethoxyethoxy)-4-Methyloct-1Z-ene The method taught in U.S. Pat. No. 4,131,737, Dec. 26, 1978, (B. F. Floyd et al, American Cyanamid Company), resulted in the preparation of the unprotected 1-iodovinyl alcohols. The method taught in U.S. Pat. No. 4,132,738, Jan. 2, 1979, resulted in the protected 1-iodovinyl alcohols. The E/Z mixture of protected iodovinyl alcohols was used as obtained. The ratio of E to Z was ca. 9:1 by $^{13}$C nmr of the intermediate 1-tri-n-butylstanyl vinyl alcohols.

(2) Preparation of Organolithiocuprates from Protected Iodovinylalcohols

The method described in Example I was used by replacing 1-iodo-3S-trimethylsilyloxyoct-1E-ene with 1-iodo-4RS-(2-ethoxyethoxy)-4-methyloct-1E-ene and 1-iodo-4RS-(2-ethoxyethoxy)-4-methyloct-1Z-ene.

B. The method described in Example I was used to prepare TR-7141 and TR-7142 by replacing the 4R-trimethylsilyloxy-2-(6-carbomethoxyhexyl)-2-cyclopenten-1-one with 4R-(2-ethoxyethoxy)-2-[7-(2-ethoxyethoxy)heptyl]-2-cyclopenten-1-one.

The resulting PGE$_1$ analog had the following spectral characteristics:

TR-7141: [α]$_D$ −62.3° (c 1.0, CHCl$_3$); R$_f$(system II) 0.40; pmr (CDCl$_3$): 0.90 (3H, 5, J=7 Hz), 1.1 (3H, s), 1.1-3.1 (26H, m), 2.1 (3H, s), 3.6 (3H, 5, J=6 Hz), 4.1 (1H, m), 5.5 (2H, m); cmr (CDCl$_3$) δ: 168.9 (C-9a), 141.7 (C-9), 133.4 (C-14), 128.2 (C-13), 127.0 (C-8), 75.0 (C-16), 72.4 (C-11), 62.7 (C-1), 57.1 (C-12), 45.0 (C-10), 41.8, 41.4 (C-16a), 23.3 (C-19), 20.6 (C-9b), 14.0 (C-20); ir (CHCl$_3$) 3600 (s), 3650-3200 (b), 2940, 1740, 1690, 1455, 1365, 1220, 1040, 965 cm$^{-1}$; ms (70 eV) 378 (p-H$_2$O), 360 (p-2H$_2$O), 336 (p-HOAc), 321 (p-HOAc-CH$_3$), 318 (p-HOAc-H$_2$O).

TR-7142: [α]$_D$ −45.9° (c 1.0, CHCl$_3$); R$_f$ (system II), 0.45; cmr (CDCl$_3$) δ: 168.6 (C-9a), 141.8 (C-9) 133.7 (C-14), 128.9 (C-8), 127.0 (C-13), 75.8 (C-16), 73.0 (C-11), 62.9 (C-1), 51.2 (C-12), 43.2 (C-10), 41.1 (C-16a), 23.3 (C-19), 20.7 (C-9b), 14.0 (C-20); pmr (CDCl$_3$) δ: 0.92 (3H, t, J=7 Hz), 1.20 (1.22) (3H, s), 1.0–3.0 (26H, m), 2.1 (3H, s), 3.6 (2H, t, J=6 Hz), 4.1 (1H, m), 5.5 (2H, m); ir (CHCl$_3$); 3700-3200 (b) 3670 (s), 2940, 1740, 1450, 1370, 1210, 1040 cm$^{-1}$; ms (70 eV) nearly identical to TR-7141.

EXAMPLE XII

Methyl 9,11α,15S-Triacetoxprosta-8,13E-Dien-1-Oate (TR-7143)

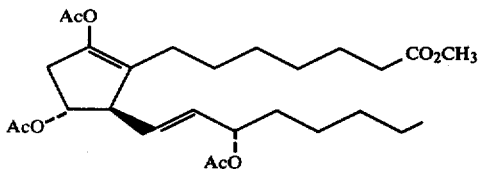

To 45 mg. TR-7091 at 0° C. was added 0.3 ml. dry pyridine and 0.3 ml. dry acetic anhydride and the mixture was allowed to stand at room temperature for 2.0 hours. The reaction mixture was added to cracked ice and diluted with ether-ethyl acetate 1:1 (v/v). The layers were separated and the organic layer was washed with 2% aqueous sulfuric acid, 10% aqueous sodium bicarbonate and brine. The organic extract was dried (MgSO$_4$), filtered and the solvents removed in vacuo to yield 48 mg. of TR-7143 as a colorless oil having the following physical characteristics:

TR-7143: [α]$_D$ −86.9° (c 1.0, CHCl$_3$); R$_f$ (system II) 0.59; pmr (CDCl$_3$) δ: 0.9 (3H, t, J=7 Hz), 1.1–3.1 (23H, m), 2.0 (6H, s), 2.1 (3H, s), 3.7 (3H, s), 4.9 (C-11-H, m), 5.2 (C-15-H, m), 5.5 (2H, m); cmr (CDCl$_3$) δ: 174.1 (C-1), 170.5 (C-11a), 170.1 (C-15a), 168.1 (C-9a), 142.6 (C-9), 131.5 (C-14), 131.1 (C-13), 126.1 (C-8), 76.4 (C-15), 74.2 (C-11), 53.1 (C-12), 51.4 (C-1a), 21.2 (C-11b), 21.1 (C-15b), 20.6 (C-9b), 13.9 (C-20); ir (CHCl$_3$) 2935, 1725, 1435, 1370, 1240, 1210, 1015, 965 cm$^{-1}$; ms (70 eV) 435 (p-C$_2$H$_3$O$_2$), 419 (p-Ac-CH$_3$OH), 393 (p-C$_5$H$_9$O$_2$), 375 (p-CO$_2$Me-HOAc), 332 (base peak) (p-CO$_2$Me-HOAc-Ac).

EXAMPLE XIII

Methyl 9,15R-Diacetoxy-11α-Hydroxyprosta-8,13E-Dien-1-Oate (TR-7132)

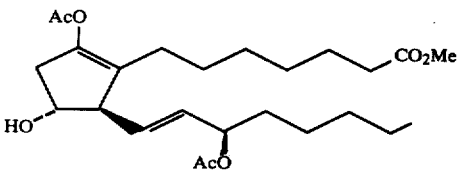

A. Preparation of Organolithiocuprate from Iodovinylalcohol

The method described in Example X was used to prepare 1-iodo-3R-trimethylsilyloxyoct-1E-ene.

B. Substituted 2-Cyclopenten-1-One

The methods taught by C. J. Sih et al [J. Amer. Chem. Soc., 97, 857 and 865 (1975)] were used to prepare 4R-(1-ethoxyethyl)-2-(6-carbomethoxyhexyl)-2-cyclopenten-1-one.

C. Prostaglandin Synthesis (1) The method described in Example I was used to prepare methyl 9-acetoxy-15R-hydroxy-11α(1-ethoxyethyl)prosta-8,13E-dien-1-oate utilizing the organolithiocuprate and substituted 2-cyclopenten-1-one described above.

(2) The resultant yellow oil was further processed as described in Example XII to yield methyl 9,15R-diacetoxy-11α-(1-ethoxyethyl)prosta-8,13E-dien-1-oate.

(3) The resultant orange oil was further processed by the method described in Kluender et al, U.S. Pat. No. 4,132,738 of Jan. 2, 1979, to remove the ethoxyethyl protecting group (65:35:10 acetic acid:water:tetrahydrofuran). The resultant oil was purified by column chromatography (silica gel, gradient elution of 8:2 (v:v) to 1:1 (v:v) hexane:ethyl acetate) and further purified by HPLC using 15% isopropanol in hexane as eluent.

In this manner 82.7 mg. of TR-7132 as a colorless oil was obtained, having the following physical characteristics: [α]$_D$ −27.5° (c 1.0, CHCl$_3$); R$_f$ (system II) 0.62; nmr (CDCl$_3$ δ: 0.88 (3H, t), 1.2 (18, m), 2.03 (3H, s), 2.14 (3H, s), 2.2–3.0 (6H, m), 3.6 (3H, s), 4.08 (1H, m), 5.4 (1H, m), 5.6 (2H, m); cmr (CDCl$_3$) δ: 174.1 (C-1), 170.2 (C-15a), 168.6 (C-9a), 142.3 (C-9), 132.5 (C-14), 131.0 (C-13), 126.3 (C-8), 74.9, 74.4, 56.6, 51.4, 13.9 (C-20); ir (CHCl$_3$) 3620-3300 (b), 2930, 1730, 1440, 1235, 1200, 970 cm$^{-1}$; ms (C.I., isobutylene) 453 (m+1), 435 (453-H$_2$O), 393 (453-HOAc), 375 (393-H$_2$O), 351 (base peak) (453-OAc-Ac).

EXAMPLE XIV

Methyl 9,15S-Diacetoxy-11α-Hydroxyprosta-8,13E-Dien-1-Oate (TR-7138)

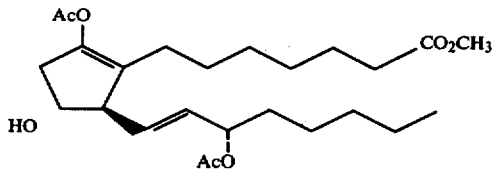

A. Preparation of Organolithiocuprate from Iodovinylalcohol

The method described in Example I was used.

B. Substituted 2-Cyclopenten-1-One

The 2-cyclopenten-1-one in Example XIII was used.

C. Prostaglandin Synthesis

The methods described in Example XIII were used to prepare TR-7138 utilizing the 2-cyclopenten-1-one described above. The resultant PGE$_1$ analog had the following physical characteristics:

TR-7138: [α]$_D$ −86.9° (c 1.0, CHCl$_2$); R$_f$ (system II) 0.59; nmr (CDCl$_3$) δ: 0.88 (3H, 6t, J=5 Hz), 1.0–1.9 (18H, m), 2.03 (3H, s), 2.14 (3H, s), 2.2–3.0 (6H, m), 3.67 (3H, s), 4.11 (1H, m), 5.22 (1H, m), 5.56 (2H, m); ir (CHCl$_3$) 3650-3250 (b), 2935, 1725, 1435, 1365, 1235, 965 cm$^{-1}$; cmr (CDCl$_3$) δ: 174.1 (C-1), 1702 (C-15a), 168.5 (C-9a), 142.4 (C-9), 132.5 (C-14), 131.1 (C-13), 126.2 (C-8), 74.8, 74.6, 56.7, 13.9 (C-20), ms (E.I.): 434 (m-H$_2$O), 420 (m-MeOH), 392 (m-CH$_3$CO$_2$H), 350 (base peak) (m-C$_5$H$_{11}$-OMe).

EXAMPLE XV

Methyl 9-Acetoxy-16,20-Methano-11α,15R Dihydroxyprosta-8,13E-Dien-1-Oate (TR-7144)

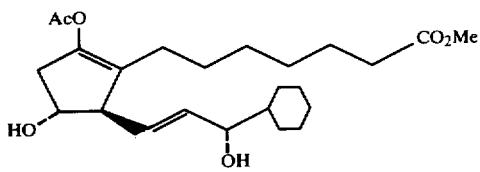

A. Preparation of Organolithiocuprate from Iodovinylalcohol

The method described in Example IV was used to prepare 1-iodo-3R-trimethylsilyloxy-3-cyclohexyl-1E-propene and its corresponding organolithiocuprate.

B. The method described in Example I was used to prepare TR-7144 replacing 1-iodo-3S-trimethylsilyloxyoct-1E-ene with 1-iodo-3R-tri-methylsilyloxy-3-cyclohexyl-1E-propene.

The resulting PGE$_1$ analog, as a white solid, had the following physical characteristics:

TR-7144: m.p. 59°–61°; [α]$_D$ −68.8° (c 1.0, CHCl$_3$); R$_f$ (system II) 0.35; nmr (CDCl$_3$) δ: 0.9–3.1 (28H, m), 2.15 (3H, s), 4.2 (2H, m), 5.6 (2H, m); ir (CHCl$_3$) 3700-3250 (b), 3600 (s), 2930, 1730, 1440, 1365, 965 cm$^{-1}$; ms (E.I.) 404 (m-H$_2$O), 363 (m-OAc), 362 (m-HOAc), 345 (363-H$_2$O), 344 (362-H$_2$O), 43 (base peak) (Ac).

EXAMPLE XVI 1,9-Diacetoxy-11α,16RS-Dihydroxy-16-Methylprosta-8,13E-Diene (TR-7151)

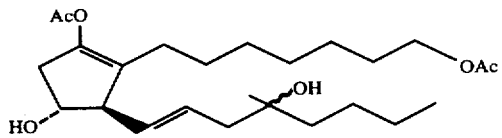

A. Preparation of Substituted 2-Cyclopenten-1-One

The reaction of 4R-hydroxy-2-[7-hydroxyheptyl]-2-cyclopenten-1-one with acetic acid in an inert solvent, such as tetrahydrofuran, ether or toluene, and an acid catalyst such as para-toluenesulfonic acid, at a temperature of from 20° to 50° for 5 to 50 hours provided the compound 4R-hydroxy-2-(7-acetoxyheptyl)-2-cyclopenten-1-one. The hydroxy group was protected by the methods familiar to those skilled in the art [see H. C. Kluender et al, *Tetrahedron Letters*, 2063, (1977)] to produce the compound 4R-(1-ethoxyethyl)-2-(7-acetoxyheptyl)-2-cyclopenten-1-one.

B. The method described in Example XI was used to prepare TR-7132 by replacing the 4R-(2-ethoxyethoxy)-2-[7-(2-ethoxyethoxy)heptyl]-2-cyclopenten-1-one with 4R-(1-ethoxyethyl)-2-(7-acetoxyheptyl)-2-cyclopenten-1-one.

The resulting PGE$_1$ analog had the following physical characteristics:

TR-5171: [α]$_D$ −39.1, (c 1.0, CHCl$_3$), R$_f$ (system II) 0.48; nmr (CDCl$_3$) δ: 0.88 (3H, bt), 1.14 (3H, s), 1.1–3.1 (25H, m), 2.04 (3H, s), 2.14 (3H, s), 4.04 (3H, bt, J=6 Hz), 5.4 (2H, m); cmr (CDCl$_3$) δ: 171.1 (C-1a), 168.6 (C-9a), 142.1 (C-9), 133.5 (C-14), 128.4 (C-13), 126.9 (C-8), 75.3 (C-16), 72.4 (C-11), 64.6 (C-1), 57.3, 14.0 (C-20); ir (CHCl$_3$) 3630–3150 (b), 2925, 1725, 1455, 1365, 1240, 1030, 965 cm$^{-1}$; ms (E.I.) 402 (m-2H$_2$O), 378 (m-HOAc), 363 (378-CH$_3$), 360 (378-H$_2$O).

EXAMPLE XVII (1-Acetoxy-11α,15S-Dihydroxyprosta-8,13E-Dien-9-yl) Hydrogen Succinate (TR-7158)

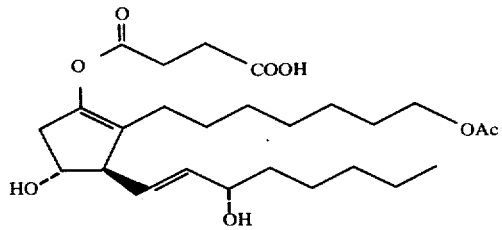

A. Substituted 2-Cyclopenten-1-one

The methods described in Example XVI were used to prepare the 4R-(1-ethoxyethyl)-2-(7-acetoxyheptyl)-2-cyclopenten-1-one.

B. The methods described in Example I were used to prepare TR-7158 by replacing 4R-trimethylsilyloxy-2-(6-carbomethoxyhexyl)-2-cyclopenten-1-one with 4R-(1-ethoxyethyl)-2-(7-acetoxyheptyl)-2-cyclopenten-1-one and the acetic anhydride with succinic anhydride. In this manner TR-7158 was obtained as an off-white solid having the following physical characteristics:

TR-7158: m.p. 64°–68° C.; [α]$_D$ −54.3° (c 1.0, MeOH); R$_f$ (system II) 0.27; nmr (CDCl$_3$) δ: 0.88 (3H, bt, J=5 Hz), 1.0–3.2 (23H, m), 1.98 (3H, s), 2.67 (4H, bs), 4.01 (4, bt, J=6 Hz), 5.5 (2H, m), 6.08 (3H, broad, D$_2$O exchangeable); cmr (CDCl$_3$) δ: 175.4 (C-9a), 171.6 (C-9a), 170.4 (C-1a), 141.8 (C-9), 135.8 (C-14), 131.5 (C-13), 126.9 (C-8), 75.0, 73.1, 64.8 (C-1), 14.0 (C-20); ir (CHCl$_3$) 3600–3200 (b), 2930, 1750, 1730, 1710, 1460, 1365, 1125, 970 cm$^{-1}$; ms (E.I.) 364 (m-(CO$_2$H)$_2$(CH$_2$)$_2$), 346 (364-H$_2$O), 304 (364-HOAc), 293 (base peak) (m-C$_5$H$_{11}$—(CO$_2$H)$_2$(CH$_2$)$_2$).

EXAMPLE XVIII (1,11α,15S,Trihydroxyprosta-8,13E-Dien-9-yl)Hydrogen Succinate (TR-7159) and Methyl (1,11α,15S-Trihydroxyprosta-8,13E-Dien-9-yl)Succinate (TR-7154)

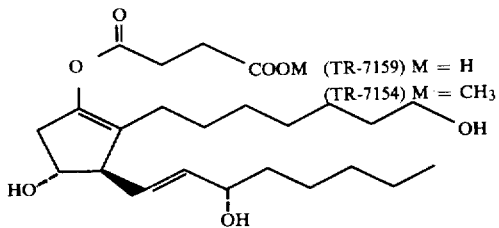

A. Substituted 2-Cyclopenten-1-one

The method described in Example IX were used to prepare 4R-(1-ethoxyethyl)-2-[7-ethoxyethyl)-heptyl]-2-cyclopenten-1-one.

B. The methods described in Example XVII were used to prepare TR-7159 by replacing 4R-(1-ethoxyethyl)-2-(7-acetoxyheptyl)-2-cyclppenten-1-one with 4R-(1-ethoxyethyl)-2-[7-(1-ethoxyethyl)-heptyl]-2-cyclopenten-1-one. TR-7159, as a white solid, has the following physical characteristics:

TR-7159: m.p. 82°-84° C., [α]$_D$ 67.5° (c b 1.0, MeOH); R$_f$ (system II) 0.17; nmr (CD$_3$OD) δ: 0.90 (3H, bt), 1.1-3.0 (23H, m), 2.67 (4H, bs), 3.54 (2H, bt, J=6.9 Hz), 4.05 (2H, m), 5.5 (2H, m); cmr (CD$_3$OD) δ: 175.4 (C-9d), 171.8 (C-9a), 142.8 (C-9), 136.6 (C-14), 131.9 (C-13), 127.7 (C-8), 75.5, 73.4, 62.9 (C-1), 14.2 (C-20); ir (CHCl$_3$) 3700-3150 (b), 2930, 1740, 1725, 1460, 1365, 1220, 1140, 970 cm$^{-1}$; ms (E.I.) 423 (m-OH), 395 (m-CO$_2$H), 351 (m-H$_2$O-C$_5$H$_{11}$), 347 (m-CO$_2$H—CH$_2$OH—OH), 322 [m(CH$_2$CO$_2$H)$_2$], 304 (322-H$_2$O), 251 (base peak) 322-C$_5$H$_{11}$).

C. Preparation of TR-7154 from TR-7159

To a solution containing TR-7159 in 1:1 (v:v) methanol:ether at 0° C., was added excess ethereal diazomethane Or. syn., (Collective Vol. V), H. E. Baumgarten Ed., pp. 351, John Wiley & Sons, (1973)]. After 15 min. at 0° C., the excess diazomethane was removed by purging with nitrogen.

The solvents were evaporated in vacuo to yield crude TR-7154 which was purified by HPLC using 20% isopropanol in n-hexane as eluant. In this manner TR-7154 was obtained as a white solid having the following characteristics:

TR-7154: m.p. 60°-61° C., [α]$_D$ −69.2° (c 1.0, CHCl$_3$); R$_f$(system II) 0.29; nmr (CDCl$_3$) δ: 0.88 (3H, bt, 1.1-3.0 (26H, m), 2.70 (4H, t, J=2.9 Hz), 3.61 (2H, 5, J=6.0 Hz), 3.70 (3H, s), 4.0 (2H, m), 5.5 (2H, m); cmr (CDCl$_3$) 181.0 (C-9d), 170.1 (C-9a), 142.0 (C-9), 135.9 (C-14), 130.7 (C-13), 126.9 (C-8), 75.1, 72.9, 62.9 (C-1), 14.0 (C-20); ir (CHCl$_3$) 3680-3200 (b) 3620 (s), 2935, 1740, 1700 (sh), 1440, 1365, 1175, 1145, 1050, 965 cm$^{-1}$; ms (E.I.) 420 (m-20H), 419 (m-H$_2$O-OH), 395 (m-CO$_2$Me), 392 (m-CH$_2$OH-Me), 365 (m—C$_5$H$_{11}$—H$_2$O), 115 (base peak) (CO(CH$_2$)$_2$CO$_2$Me).

EXAMPLE XIX (1,11α,15S-Trihydroxyprosta-8,13E-Dien-9-yl) Hydrogen Adipate (TR-7165)

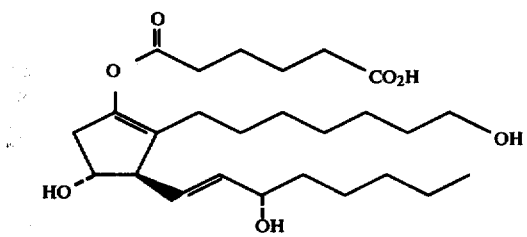

A. The methods described in Example XVIII were used to prepare Tr-7165 with the exception that monomeric adipic anhydride [J. W. Hill, J. Amer. Chem. Soc., 52, 4110 (1930)] was used in lieu of succinic anhydride. In this manner TR-7165 was obtained having the following physical characteristics:

TR-7165: [α]$_D$ −48.3° (c 1.48, MeOH); R$_f$(system II) 0.23; nmr ((CD$_3$)$_2$CO)) δ: 0.88 (3H, bt), 1.0-3.0 (31H, m), 3.5 (2H, t, J=5.9 Hz), 4.1 (6H, m), 5.5 (2H, m); cmr ((CD$_3$)$_2$CO)) δ: 174.5 (C-9a), 171.4 (C-9f), 143.1 (C-9), 137.1 (C-14), 127.1 (C-13), 127.1 (C-8), 75.4, 72.8, 62.4 (C-1), 14.3 (C-20); ir (KBr) 3700-3200 (s), 2930, 1700, 1450, 1165, 1015, 970 cm$^{-1}$; ms (E.I.) 450 (m-H$_2$O), 433 (450-OH), 414 (m-3H$_2$O), 322 (m-(CO$_2$H)$_2$(CH$_2$)$_4$), 95 (base peak) (C$_5$H$_3$O$_2$).

EXAMPLE XX

Methyl 9-Acetoxy-17,17-Dimethyl-11α,16S-Dihydroxyprosta-8,13E-Dien-1-Oate (MLS-7167) and Methyl 9-Acetoxy-17,17-Dimethyl-11α,16R-Dihydroxyprosta-8,13E-Dien-1-Oate (MLS-7168)

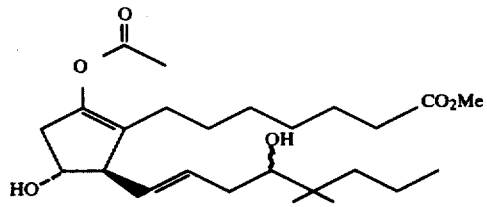

A. Preparation of Organolithiocuprate from Iodovinylalcohol (1) The methods described in Kluender et al, U.S. Pat. No. 4,132,738, Jan. 2, 1979, were used to prepare the organolithiocuprate from 1-iodo-4RS-hydroxy-5,5-dimethyl-1E-octene.

B. Using the methods described in Example XIII but substituting the above described organolithiocuprate for the organolithiocuprate used in Example XIII (obviating the second acylation step), MLS-7167 and MLS-7168 were isolated as yellow oils having the following physical characteristics:

MLS-7167: [α]$_D$ −48.7° (c 1.0, CHCl$_3$); R$_f$(system II) 0.52; nmr (CDCl$_3$) δ: 0.85 (3H, s), 0.87 (3H, s), 0.89 (3H, t, J=5.1 Hz), 1.3-3.3 (23H, m), 2.14 (3H, s), 3.66 (3H, s), 4.14 (2H, m), 5.5 (2H, m); cmr (CDCL$_3$) δ: 174.2 (C-1), 168.7 (C-9a), 142.0 (C-9), 132.5 (C-14), 130.8 (C-13), 126.8 (C-8), 77.6 (C-16), 75.3 (C-11), 57.1 (C-12), 14.2 (C-20); ir (CHCl$_3$) 3650-3200 (b), 2935, 1740, 1460, 1440, 1365, 1220, 970 cm$^{-1}$; ms (E.I. as di-TMS derivative) 567 (m-CH$_3$), 509 (m-TMS), 482 (567-(CH$_3$)$_2$(CH$_2$CH$_2$CH$_3$), 43 (base peak) (Ac).

MLS-7168: [α]$_D$ −58.6° (c 1.0, CHCl$_3$); R$_f$(system II) 0.51, nmr, ir and ms nearly identical to TR-7167.

EXAMPLE XXI 1,11α,15S-Trihydroxy-9-(1-Acetyl-4-Piperidenecarboxy)Prosta-8,13E-Diene (MLS-7169) and 1,11α,15S-Trihydroxy-9-[(2-Methylpropyl)-Carbonyldioxy]prosta-8,13E-Diene (MLS-7170)

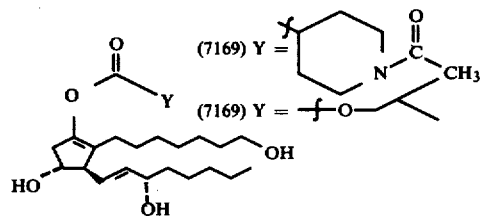

A. Preparation of Organolithiocuprate from Iodovinylalcohol

The methods described in Example I were used to prepare the organolithiocuprate from 1-iodo-3S-hydroxyoct-1E-ene protected as the tetrahydropyranyl ether.

B. Preparation of the Mixed Anhydride: 2-Methylpropyl-Carbonyldioxy-4-Carbonyl-1-Acetylpiperidine from 1-Acetyl-4-Piperidinecarboxylic Acid To 533 mg. 1-acetyl-4-iperidinecarboxylic acid (Aldrich) in 10 ml. dry tetrahydrofuran, under argon, was added 0.54 ml. triethylamine. The mixture was cooled to 0° C. whereupon 0.48 ml. of isobutyl chloroformate (Aldrich) was added dropwise over a 2 min. period. After 1.5 hrs. at 0° C. the reaction mixture was filtered through a sintered glass funnel containing a pad of Celite ®. The pad was washed with ether and the filtrate was evaporated in vacuo to yield 686 mg. (81%) of 2-methyl-propylcarbonyldioxy-4-carbonyl-1-acetyl-piperidine as a colorless oil. This material, having the following spectral characteristics, was used as obtained in the subsequent reaction.

NMR (CDCl$_3$) δ: 0.95 (6H, d, J=7 Hz), 2.1 (3H, s), 4.0 (1H, d, J=6 Hz); ir (CHCl$_3$) 3000, 2960, 1820, 1750 (sh), 1630, 1450, 1245, 1090, 975 cm$^{-1}$.

C. The methods described in Example IX were used to prepare MLS-7169 and MLS-7170 substituting the above described organolithiocuprate and mixed anhydride for the organolithiocuprate and isobutyryl chloride, respectively. In this manner MLS-7169 and the side product MLS-7170 were obtained as an orange oil and white solid, respectively, having the following physical characteristics:

MLS-7169: [α]$_D$ −46.4° (c 0.97, CHCl$_3$); R$_f$ (system II) 0.11; R$_f$ (acetone) 0.23; nmr (CDCl$_3$) δ: 0.88 (3H, bt, J=5.9 Hz), 1.0–3.3 (34H, m), 2.17 (3H, s), 3.2 (2H, bt, J=5.9 Hz), 4.05 (2H, m), 4.4 (1H, bdt, J=13.8, 4.2 Hz), 5.6 (2H, m); ir (CHCl$_3$) 3700–3200 (b), 3600 (s), 2930, 1740, 1690, 1630, 1450, 1370, 1175, 1145, 965, 900 cm$^{-1}$; ms (E.I.) 475 (m-H$_2$O), 458 (475-OH), 457 (m-2H$_2$O), 432 (475-Ac), 415 (475-HOAc), 404 (475-C$_4$H$_{11}$), 112 (base peak) [(CH$_2$)$_4$NCO].

MLS-7170: [α]$_D$ −58.4° (c 1.25, CHCl$_3$): R$_f$ (system II) 0.47; nmr (CDCl$_3$) δ: 0.88 (3H, t), 0.97 (6H, d, J=6.8 Hz), 1.1–3.2 (27H, m), 3.60 (2H, t, J=7.1 Hz), 3.96 (2H, d, J=6.6 Hz), 4.09 δ (2H, m), cmr (CDCl$_3$) δ: 153.0 (C-9a), 141.8 (C-9), 136.0 (C-14), 131.1 (C-13), 126.9 (C-8), 74.8 (C-11), 74.6 (C-9b), 72.9 (C-15), 62.7 (C-1), 56.6 (C-12), 38.9 (C-7), 14.0 (C-20); ir (CHCl$_3$) 3650–3300 (b), 3620 (s), 2935, 1750, 1365, 1340, 1205, 1040, 965 cm$^{-1}$; ms (E.I.) 422 (m-H$_2$O), 404 (m-2H$_2$O), 323 (m-OCOCH$_2$-CH(CH$_3$)$_2$), 278 (323-OH$_2$OH), 57 (base peak) (CH$_2$CH(CH$_3$)$_2$).

EXAMPLE XXII 1,11α,15R-Trihydroxy-9-(11-Acetoxy-3,6,9-Trioxyundecanoate)prosta-8,13E-Diene (MLS-7171) and
1,11α,15S-Trihydroxy-9-(11-Acetoxy-3,6,9-Trioxyundecanoate)prosta-8,13E-Diene (MLS-7172)

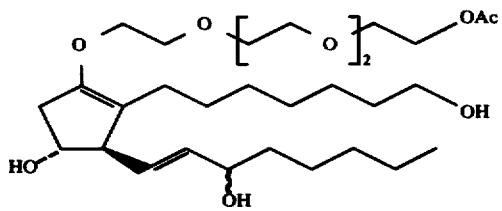

A. Preparation of Organolithiocuprate from Iodovinylalcohol

The methods described in Example IX were used by replacing 1-iodo-3R-(1-ethoxyethyl)-3-cyclohexyl-1E propane with 1-iodo-3RS-(1-ethoxyethyl-1E-octene [A. F. Kluge et al, J. Amer. Chem. Soc., 94, 7827 (1972)].

B. Preparation of 11-Acetoxy-3,6,9-Trioxyundecanoyl-Carbonyl-Dioxy-2-Methylpropane from Tetraethylene Glycol (1) 11-Acetoxy-3,6,9-Trioxyundecanol The procedure adapted from A. Shanzer Tetrahedron Letters, 221 (1980) was used. To 39.8 g. di-n-butyl tin oxide (Alfa Ventron) in 75 ml. toluene, under argon, was added 29.1 g. tetraethylene glycol (Aldrich). The mixture was stirred at reflux overnight collecting the water produced in a Dean Stark trap. The toluene was removed by distillation and the remaining orange oil was diluted with 75 ml. chloroform. To the refluxing solution was added, dropwise over a 0.5 hr. period, 10.7 ml. acetyl chloride in 150 ml. chloroform. After addition was complete the reaction mixture was refluxed for an additional 0.75 hr. The reaction mixture was cooled to room temperature and 100 ml. 10% aqueous sodium bicarbonate was added. The resultant emulsion was filtered through Celite ® and the organic layer of the filtrate dried (MgSO$_4$). The filtrate was evaporated in vacuo to yield 19.0 g. of crude product as a yellow oil.

The crude reaction product was placed on a sintered glass funnel containing 520 ml. silica gel and eluted with mixtures of methylene chloride to 4:6 (v:v) methylene chloride-acetone (500 ml. fractions). Those fractions containing product (R$_f$ (2:1 (v:v) acetone:chloroform) 0.33) were evaporated in vacuo to yield 11-acetoxy-3,6,9-trioxyundecanol as a colorless oil having the following spectral characteristics:

NMR (CDCl$_3$) δ: 2.0 (3H, s), 3.1 (1H, bs, D$_2$O exchangeable), 3.7 (14H, bt, J=5 Hz), 4.2 (2H, m); ir (CHCl$_3$) 3700–3200 (b), 3600 (s), 3010 (s), 2875, 1730, 1450, 1250, 1125, 1055 cm$^{-1}$.

(2) 11-Acetoxy-3,6,9-Trioxyundecanoic Acid

To 3.8 g. 11-acetoxy-3,6,9-trioxyundecanol in 50 ml. acetone at −30° C. was added 23.0 ml. of 1.4 M Jones Reagent [Reagents for Organic Synthesis (Vol. 1), L. F. Fieser and M. Fieser, p. 142, John Wiley & Sons, New York (1967)]. The reaction mixture was warmed to −25° C. and stirred at this temperature for 1.0 hr. The reaction mixture was quenched by the addition of 2.5 ml. isopropanol. To the reaction mixture was added 120 ml. of ether and 5.7 g. Celite ®. The reaction mixture was filtered through a sintered glass funnel containing a pad of Celite ® and the pad washed with several portions of ether. The filtrate was basified to pH 8 by the addition of triethylamine and the solvents evaporated in vacuo. The residue was diluted with 1:1 (v:v) ether-:ethyl acetate and cooled to 0° C. whereupon 3 N hydrochloric acid was added until a pH 3–4 was obtained. The layers were separated and the organic layer washed with saturated aqueous brine and dried (MgSO$_4$). After evaporation of solvents in vacuo the dark green oil was placed on a sintered glass funnel containing 25 ml. silica gel and eluted with methylene chloride to 1:1 methylene chloride:acetone as eluant (50 ml. fractions). Those fractions which contained the desired products (R$_f$ (2:1:0.1) (v:v:v) acetone:methanol:acetic acid) 0.21) were pooled together and the solvents evaporated in vacuo to yield 11-acetoxy-3,6,9-trioxyundecanoic acid, as a colorless oil, having the following spectral characteristics:

NMR (CDCl$_3$) δ: 2.1 (3H, s), 3.7 (10H, m), 4.2 (4H, m), 8.0 (1H, D$_2$O exchangeable); ir (CHCl$_3$) 3620–3050 (b), 2915, 1735, 1450, 1365, 1240, 1120, 1050 cm$^{-1}$.

(3) 11-Acetoxy-3,6,9-Trioxyundecanoylcarbonyldioxy-2-Methylpropane

The method described in Example XXI was used to prepare this mixed anhydride by substituting 11-acetoxy-3,6,9-trioxyundecanoic acid in lieu of 1-acetyl-4-piperidinecarboxylic acid. The resultant 11-acetoxy-3,6,9-trioxyundecanoyl-carbonyl-dioxy-2-methylpropane, as a yellow-orange oil, was used as obtained in the subsequent reaction and had the following spectral characteristics:

NMR (CDCl$_3$) δ: 1.0 (6H, d, J=6.5 Hz), 1.2 (1H, J=6.5 Hz), 2.0 (3H, s), 3.7 (10H, m), 4.2 (6H, m).

C. Prostaglandin Synthesis

Using the methods and substituted 2-cyclopenten-1-one of Example IX but substituting the organolithiocuprate above for the one used in Example IX and 11-acetoxy-3,6,9-trioxyundecanoyl-carbonyldioxy-2-methylpropane for isobutyryl chloride, MLS-7171 and MLS-7172 were obtained as off-white waxy solids having the following physical characteristics:

MLS:7172: [α]$_D$ −45.7° (c 0.84, CHCl$_3$); R$_f$(system II) 0.08; nmr (CDCl$_3$) δ: 0.88 (3H, t, J=5.7 Hz), 1.0–3.2 (26H, m), 2.08 (3H, s), 3.73 (12H, m), 4.26 (6H, m), 5.47 (2H, m); ir (CHCl$_3$) 3740–3100 (b), 3600 (s), 2935, 1730, 1700 (sh), 1460, 1255, 1210, 1110, 970 cm$^{-1}$; cmr (CDCl$_3$) δ: 168.3 (C-9a), 141.6 (C-9), 136.0 (C-14), 130.3 (C-13), 127.1 (C-8), 75.0 (C-15), 72.8 (C-11), 71.1 (C-9b), 70.7 (C-9d and 9f), 70.5 (C-9e), 69.2 (C-9g), 68.4 (C-9c), 63.7 (C-9h), 62.9 (C-1), 56.7 (C-12), 14.0 (C-20); ms (E.I.) 536 (m-2H$_2$O), 483 (m-H$_2$O-C$_5$H$_{11}$), 451 (483-CH$_3$OH), 87 (base peak) [(CH$_2$)$_2$OAc].

MLS-7171: [α]$_D$ −33.7° (c 0.78, CHCl$_3$); R$_f$(system II) 0.12, nmr, ir, ms nearly identical to TR-7172.

EXAMPLE XXIII

9-Acetoxy-11α,15R-Dihydroxy-16,16-Dimethylprosta-5Z,8,13E-Trienoic Acid (MLS-7174) and
9-Acetoxy-11α,15S-Dihydroxy-16,16-Dimethylprosta-5Z,8,13E-Trienoic Acid (MLS-7175)

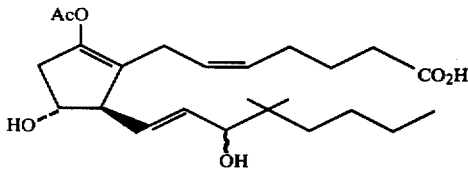

A. Substituted 2-Cyclopenten-1-one (1) Preparation of 4R-hydroxy-2-(6-Carboxyhex-3Z-enyl)-2-Cyclopenten-1-one A solution containing 998 mg. 4R-hydroxy-2-(6-carboethoxyhex-3Z-enyl)-2-cyclopenten-1-one [C. J. Sih et al, Tetrahedron Letters 2313 (1973)] in 2 ml. ethanol was added to a stirred (ph 8.0) solution of 500 ml. of 0.1 M potassium phosphate buffer containing 575 units (0.6 ml.) of Hog liver esterase (Sigma) (EC 3.1.1.1). After 18 hrs. (overnight) the solution was reduced in volume (rotoevaporator), diluted with ethyl acetate and the rapidly stirred mixture carefully acidified to pH 3.5 by the dropwise addition of 3 N hydrochloric acid. The organic layer was separated, washed with saturated aqueous brine and dried (MgSO$_4$). The aqueous solutions were back extracted with ethyl acetate and the combined, dried, organic filtrate evaporated in vacuo to yield 747 mg. of crude product as an orange oil. Although pure enough for further transformation, this material was column chromatographed on 100 ml. silica gel using 1:1 (v:v) hexane:ethyl acetate (+0.1% acetic acid) as eluant (10 ml. fractions). In this manner 649 mg. (73%) of pure 4R-hydroxy-2-(6-carboxyhex-3Z-enyl)-2-cyclopenten-1-one as an orange oil was obtained having the following physical characteristics:

[α]$_D$ +10.0° (c 0.96, methanol), R$_f$(system II) 0.28; nmr (CDCl$_3$) δ: 1.69 (2H, bq, J=7 Hz), 1.95–2.52 (4H, m), 2.48 (1H, dd, J=5.7, 0.3 Hz), 2.73 (1H, dd, J=5.2, 0.3 Hz), 2.91 (2H, m), 4.1 (1H, d, d, d, J=5.7, 7.8 0.3 Hz), 5.5 (4H, m), 6.1 (2H, D$_2$O exchangeable), 7.2 (1H, dd, J=2.8, 0.5 Hz); cmr (CDCl$_3$) δ: 206.1 (C-9*), 178.3 (C-1), 156.4 (C-12), 146 (C-8), 131.3 (C-6), 125.5 (C-5), 68.5 (C-11), 44.8 (C-10), 33.2 (C-2), 26.3 (C-7), 24.3 (C-4), 22.7 (C-3); ir (CHCl$_3$) 3630–3100 (b), 2935, 1725 (sh), 1705, 1645, 1405, 1215, 1035 cm$^{-1}$, ms (E.I.) 224 (m), 206 (m-H$_2$O), 188 (m-2H$_2$O), 91 (base peak) [(CH$_2$($_3$CO$_2$]. *Prostaglandin numbering.

(2) Preparation of 4R-Trimethylsilyloxy-2-(6-Carbotrimethylsilyloxyhex-3Z-enyl)-2-Cyclopenten-1-one The method described in Example I was used by substituting 4R-hydroxy-2-(6-carboxyhex-3Z-enyl)-2-cyclopenten-1-one for 1-iodo-3S-hydroxyoct-1E-ene. The resultant orange oil (96%) (R$_f$(ethyl acetate) 0.45) was immediately used, as obtained, in the following reaction.

B. Prostaglandin Synthesis

The methods described in Example VI were used by substituting the substituted 2-cyclopenten-1-one described above for 4R-trimethylsilyloxy-2-(6-carbomethoxyhexyl)-2-cyclopenten-1-one. In this manner MLS-7174 and MLS-7175 were obtained as yellow oils having the following physical characteristics:

MLS-7174: [α]$_D$ −72.7° (c 1.08, CHCl$_3$); R$_f$(system II) 0.46; nmr (CDCl$_3$) δ: 0.82 (3H, s), 0.87 (3H, s), 0.89 (3H, t, J=7 Hz), 1.23 (6H, m), 1.69 (2H, bq, J=6.8), 2.15 (3H, s), 1.9–3.19 (7H, m), 3.83 (H$_{15}$, d, J=6 Hz), 4.08 (1H, d, d, d, J=3.7, 3.2, 2.9 Hz), 5.0 (3H, b, D$_2$O exchangeable), 5.39 (2H, bt, J=6.1 Hz), 5.60 (2H, m); cmr (CDCl$_3$) δ: 177.8 (C-1), 168.9 (C-9a), 142.2 (C-9), 132.2 (C-14), 130.0 (C-13), 126.3 (C-8), 125.1 (C-6), 75.8 (C-11), 74.7 (C-15), 56.5 (C-12), 14.1 (C-20); ir (CHCl$_3$) 3700–3200 (b), 3650 (s), 2955, 2935, 1740, 1710, 1370, 1190, 1040, 970 cm$^{-1}$; ms (E.I.) 386 (m-2H$_2$O), 362 (m-HOAc), 344 (362-H$_2$O), 43 (base peak) (Ac).

MLS-7175: [α]$_D$−117.1° (c 1.14, CHCl$_3$); R$_f$(system II) 0.50; nmr, ir, ms nearly identical to MLS-7174.

EXAMPLE XXIV

9-Acetoxy-11α,15S-Dihydroxyprosta-8,13E-Dienoic Acid (MLS-7176)

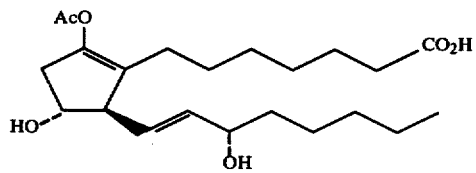

A. Substituted 2-Cyclopenten-1-one (1) Preparation of 4R-Hydroxy-2-(6-Carboxyhexyl)-2-Cyclopenten-1-one Using the methods of Example XXIII and substituting 4R-hydroxy-2-(6-carbomethoxyhexyl)-2-cyclopenten-1-one for 4R-hydroxy-2-(6-carboethoxyhex-3Z-enyl)-2-cyclopenten-1-one, the title compound was obtained as a white solid having the following physical characteristics:

[α]$_D$+15.4° (c 1.15, methanol); m.p. 35°–37° C., NMR (CDCl$_3$) δ: 1.38 (8H, m), 2.52–1.98 (5H, m), 2.84 (1H, dd, J=18.8, 5.9 Hz), 5.0 (1H, d, d, d, J=5.9, 3.4, 2.2 Hz), 6.6 (2H, D$_2$O exchangeable), 7.18 (1H, dd, J=2.2, 0.6 Hz); ir (CHCl$_3$) 3630–3250 (b), 3600 (s), 2935, 1705, 1630 (sh), 1410, 1230, 1030, 940 cm$^{-1}$, ms (E.I.) 226 (m), 208 (m-H$_2$O), 190 (m-2H$_2$O), 95 (base peak).

(2) Preparation of 4R-Trimethylsilyloxy-2-(6-Carbosilyloxyhexyl)-2-Cyclopenten-1-one The method described in Example XXIII was used to prepare this protected substituted 2-cyclopenten-1-one, as a colorless oil, by substituting 4R-hydroxy-2-(6-carboxyhexyl)-2-cyclopenten-1-one for 4R-hydroxy-2-(6-carboxyhex-3Z-enyl)-2-cyclopenten-1-one.

B. The method used in Example XXIII was used to prepare MLS-7176 by substituting 4R-trimethylsilyloxy-2-(6-carbosilyloxyhexyl)-2-cyclopenten-1-one for 4R-trimethylsilyloxy-2-(6-carbotrimethylsilyloxyhex-3Z-enyl)-2-cyclopenten-1-one. The analog, MLS-7176, as an orange oil, had the following physical characteristics:

MLS-7176: [α]$_D$−64.1° (c 0.99, CHCl$_3$); R$_f$ (system II) 0.35; nmr (CDCl$_3$) δ: 0.80 (3H, bt, J=6 Hz), 1.0–3.2 (23H, m), 2.15 (3H, s), 4.10 (2H, m), 5.07 (3H, b, D$_2$O exchangeable), 5.5 (2H, m); cmr (CDCl$_3$) δ: 168.8 (C-9a), 142.1 (C-9), 135.7 (C-14), 130.9 (C-13), 126.5 (C-8), 75.0 (C-11), 73.0 (C-15), 56.6 (C-12), 14.0 (C-20); ir (CHCl$_3$) 3700–3150 (b), 3600 (s), 2935, 1740, 1710, 1370, 1210, 965, 900 cm$^{-1}$, ms (E.I.) 336 (m-CH$_3$CO$_2$H), 318 (336-H$_2$O), 292 (m-OAc-CO$_2$H), 43 (base peak) (Ac).

EXAMPLE XXV

9-Acetoxy-1,11α,15S-Trihydroxyprosta-9,13E-Diene (TR-7130)

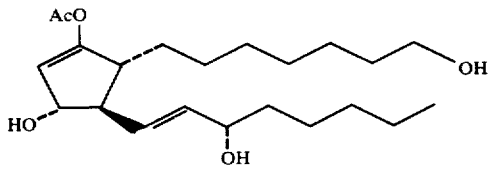

A. Preparation of 1,11R,15S-Trisilyloxyprost-13E-9-one

To 288 mg. of 1,11R,15S-trihydroxyprost-13E-en-9-one (Upjohn U.S. Pat. No. 3,636,120 of Jan. 18, 1972) was added 0.3 ml. dry tetrahydrofuran (THF) and 1.0 ml. bis-trimethylsilyltrifluoroacetamide (BSTFA) (Aldrich). The mixture was allowed to stand at room temperature for 15 hrs. at which time the reaction was judged complete by tlc. The reaction mixture was evaporated in vacuo to yield 1,11R,15S-trisilyloxyprost-13E-9-one as a yellow oil (R$_f$[CHCl$_3$] 0.52). This material was used as obtained in the subsequent transformation.

B. Prostaglandin Analog Synthesis

To 0.61 ml. of dry di-isopropylamine (Aldrich) in 2.0 ml. dry THF, at −78° C., under argon, was added 1.7 M n-butyllithium in n-hexane (Aldrich) (2.53 ml., 4.3 mmol). The resultant solution was stirred at −78° C. for 15 min. To this solution was immediately added a solution containing 400 mg. of 1,11R,15S-trisilyloxyprost-13E-9-one in 0.65 ml. dry THF. The reaction mixture was stirred at −78° for 15 min. and quenched at −78° by the addition of 0.5 ml. dry acetic anhydride. The resultant mixture was stirred at −78° for 5 min. and at −20° for 5 min. To this reaction mixture was added 15 ml. ethanol and 4 ml. of 10% aqueous hydrochloric acid. The reaction mixture was stirred at 30°–40° for 20 min. The reaction mixture was reduced in volume (rotoevaporator). The oily residue was diluted with 1:1 (v:v) ether: ethyl acetate and water. The organic phase was separated, washed with saturated aqueous sodium bicarbonate and brine and dried (MgSO$_4$). Evaporation of solvents in vacuo resulted in 211 mg. of an orange oil. This oil was purified by silica gel column chromatography using 6:4 (v:v) ethyl acetate-hexane as eluant. In this manner 28 mg. of the prostaglandin PGE$_1$ analog, TR-7130, was obtained having the following spectral characteristics:

[α]$_D$−1.3° (c 1.01, CHCl$_3$); R$_f$ (system II) 0.28; pmr (CDCl$_3$) δ: 0.9 (3H, bt, J=7 Hz), 1.3 (26H, m), 2.2 (3H, s), 2.9 (C$_{12}$-H, C$_{14}$H, C$_{10}$-H, m); cmr (CDCl$_3$) δ: 168.1 (C-9a), 154.0 (C-9), 134.7 (C-14), 132.5 (C-13), 114.7 (C-10), 78.9 (C-15), 72.9 (C-11), 62.9 (C-1), 56.2 (C-12); ir (CHCl$_3$) 3650–3200 (b), 3600 (s), 2930, 2850, 1750, 1365, 1180, 1000, 965 cm$^{-1}$; ms (70 eV) no parent, 365 (p-H$_2$O), 346 (p-2H$_2$O), 322 (p-HOAc), 304 (322-H$_2$O), 293 (p-C$_5$H$_{11}$-H$_2$O), 278 (p-(CH$_2$)$_2$OH-OAc), 252 (p-OAc-C$_5$H$_{11}$), 71 (base peak) (C$_5$H$_{11}$).

EXAMPLE XXVI

9-Acetoxy-16-Methyl-1,11α,16-RS-Trihydroxyprosta-9,13E-Diene (MLS-7177)

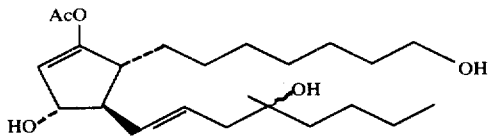

Using the methods of Example XXV and substituting 1,11R,16R,S-trihydroxy-16-methylprost-13E-en-9-one (Miles U.S. Pat. No. 4,132,738 of Jan. 2, 1979) for 1,11R,15S-trihydroxyprost-13E-en-9-one, MLS-7177 was obtained as an orange oil after further purification by HPLC (95:5 v/v ethyl acetate-ethanol).

MLS-7177: [α]$_D$−1.9° (c 1.14, CHCl$_3$); R$_f$ (system II) 0.65; pmr (CDCl$_3$) δ: 0.91 (3H, bt, J=6 Hz), 1.15 (3H, s), 1.3 (18H, m0, 1.89 (3H, D$_2$O exchangeable), 2.16 (3H, s), 2.29–2.64 (4H, m), 3.62 (2H, t, J=6 Hz), 4.47 (1H, m), 5.58 (3H, m); cmr (CDCl$_3$) δ: 168.1 (C-9a), 154.1 (C-9), 135.5 (C-13), 127.1 (C-14), 114.8 (C-10), 79.1 (C-11), 72.5 (C-16), 62.9 (C-1), 56.8 (C-12); ir (CHCl$_3$); 3560 (s), 3600–3200 (b), 2920, 2840, 1750, 1365, 1190, 1015, 965 cm$^{-1}$; ms (70 eV) no parent, 378 (p-H$_2$O), 363 (378-CH$_3$), 360 (p-2H$_2$O), 337 (p-OAc), 336 (p-HOAc), 320 (337-OH), 43 (base peak) (Ac).

EXAMPLE XXVII

Methyl 9-Acetoxy-1,11α,16S-Trihydroxy-17,17-Dimethylprosta-8,13E-Diene (MLS-7195) and 9-Acetoxy-1,11α,16R-Trihydroxy-17,17-Dimethylprosta-8,13E-Diene (MLS-7196)

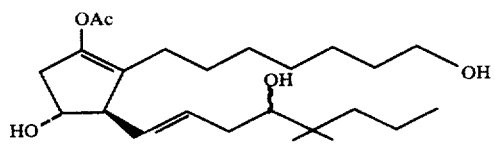

A. Preparation of Organolithiocuprate from Iodovinylalcohol

The procedures disclosed in U.S. Pat. No. 4,132,738 issued Jan. 2, 1979 were used to prepare the organolithiocuprate from 1-iodo-4-RS-hydroxy-5,5-dimethyloct-1E-ene.

B. The procedures described in Example XI were used by replacing the organolithiocuprate described in Example XI with the organolithiocuprate prepared in A above. In this manner MLS-7195 and MLS-7196 were obtained as yellow oils after purification by column chromatography and HPLC (85:15 v:v hexane-isopropanol as eluant).

MLS-7195: $[\alpha]_D - 32.9°$ (c 1.0, CHCl$_3$); R$_f$(system II) 0.48; pmr (CDCl$_3$) δ 0.85 (3H, s) 0.87 (3H, s), 0.90 (3H, bt) 1.0–3.49 (24H, m), 2.1 (3H, s), 3.62 (2H, t, J=6 Hz), 4.1 (2H, m), 5.5 (2H, m); cmr (CDCl$_3$) δ: 167.6 (C-9a), 140.4 (C-9), 131.6 (C-13), 129.7 (C-14), 125.8 (C-8), 7.63 (C-16), 73.8 (C-11), 61.4 (C-1), 55.7 (C-12), 40.5 (C-10), 21.9 (C-96), 19.4 (C-12), 15.8 (C-17), 13.9 (C-20); ir (CHCl$_3$) 3600–3050 (6), 3560 (s), 2905, 2840, 1740, 1685, 1365, 1220, 1030, 965 cm$^{-1}$.

MLS-7196: $[\alpha]_D - 41.3°$ (c 1.0, CHCl$_3$); R$_f$(system II) 0.48; nmr, is nearly identical to MLS-7195.

EXAMPLE XXVIII

Methyl 9-Acetoxy-11α,16R-Dihydroxy 17,17-Propanoprosta-8,13E-Dien-1-Oate (MLS-7198)

A. Preparation of Organolithiocuprate from Iodovinylalcohol

The procedures disclosed in U.S. Pat. No. 4,275,224 issued June 23, 1981 were used to prepare the organolithiocuprate from 1-iodo-4RS-hydroxy-5,5-propanooct-1E-ene.

B. The procedures described in Example XX were used by replacing the organolithiocuprate described in Example XX with the organocuprate described in A above. In this manner MLS-7198 was synthesized as a yellow oil and separated from its more nonpolar epimer [R$_f$(ethyl acetate) 0.59] by purification through column chromatography and HPLC (7:3 v:v ethyl acetate-hexane as eluant).

MLS-7198: $[\alpha]_D - 45.4°$ (c 1.0, CHCl$_3$); R$_f$(system II) 0.67; R$_f$(ethyl acetate) 0.58; pmr (CDCl$_3$) δ: 0.86 (3H, bt) 1.0–3.49 (29H, m), 2.1 (3H, s), 3.58 (3H, s), 4.01 (2H, m) 5.38 (2H, m); cmr (CDCl$_3$) δ: 174.2 (C-1), 168.7 (C-9a), 141.8 (C-9), 132.8 (C-13), 130.6 (C-14), 126.8 (C-8), 75.1 (C-11), 57.0 (C-12), 51.4 (C-10), 14.9 (C-20); ir (CHCl$_3$) 3600–3045 (b), 3620 (s), 2925, 2840, 1740, 1690 (sh), 1435, 1365, 1215, 1065, 965 cm$^{-1}$.

EXAMPLE XXIX

Stability Comparison of Enol Acylate Prostaglandins Analogs to Their Corresponding E Class Prostaglandins A. Stability of TR-7099 Compared to 1,11α,15S-Trihydroxyprost-13E-en-9-one (TR-4161) at 66° C.

To a thermally regulated oil bath at 66° C. was stored two 1 dram, septum sealed, vials containing solution A and solution B, respectively. Solution A contained the enol acetate analog TR-7099 (1 mg./ml.) in 1:1 (v:v) ethanol: 0.15 M potassium phosphate (pH 6.4) buffer. Solution B contained the corresponding, "daughter analog", TR-4161, at the same concentration and solvent mixture. Aliquots were taken at hour intervals and analyzed by analytical reverse phase HPLC using 40% acetonitrile in water (2 ml./min.) as eluant. Detection of HPLC peaks was determined by a Waters, Assoc. U.V. detector (210 nm) using benzhydrol as the internal standard. The loss of TR-7099 and TR-4161, respectively, were plotted by peak area vs. time. Also noted was the gain, versus time, of the A class analog TR-7059 (1,15S-dihydroxyprosta-10,13E-dien-9-one) the common acid hydrolysis by-product. The results obtained showed the loss of TR-7099 as 0.5%/hr. and the loss of TR-4161 as 2.7%/hr. Thus, TR-7099, under the above-described conditions, is at least 5.4 times more stable than the corresponding E class (daughter) analog TR-4161.

B. Stability, in vitro, of TR-7110 and TR-7111, in the presence of lipase from Rhizopus delemar To 10 mg. of a 2:1 mixture (by TLC) containing TR-7110 and TR-7111, respectively, in 2 ml. of 1:1 (v:v) ethanol: 0.1 M potassium phosphate buffer (pH 7.4) was added 0.2 mg. lipase R.delemar (Marschall Division, Research Products, Miles Laboratories, Inc.). The stirred reaction mixture, at room temperature, was monitored by TLC (system II). After 1.2 hrs. no starting material was observed but, rather, two more polar product spots (also ca. 2:1 ratio respectively). The reaction mixture was reduced in volume, diluted with ethyl acetate-ether [1:1 (v:v)] and acidified to pH 2 with 3 N hydrochloric acid. The organic layer was washed with saturated aqueous brine and dried (MgSO$_4$). The filtrate was evaporated in vacuo to yield 8.5 mg. of a pale yellow oil [R$_f$(system II) 0.33 and 0.37]. By nmr analysis of the crude reaction product, no signals at 2.2 δ (acetate) and 3.75 δ (methyl ester) was observed thus demonstrating the loss of these structural moieties from the parent compounds. The nmr spectrum also showed the presence of three D$_2$O exchangeable protons (carboxylic acid and two hydroxyl groups) and other signals attributed to E$_1$ class prostaglandin compounds. This in vitro experiment thus demonstrates that an esterase is able to hydrolyze both the C-1 ester and the C-9 enol acylate moieties and converting these compounds to their respective E class prostaglandins.

C. Stability, in vitro, of TR-7130 in the presence of Lipase from R-delemar

To. 1.1 mg. TR-7130 in a stirred solution containing 0.1 ml. ethanol and 0.5 ml. of potassium phosphate buffer (pH 7.4, 0.1 M) was added 1.0 mg. lipase from R.delemar. A TLC of the reaction mixture after 7 min. showed no starting material (R$_f$ (system II) 0.31) but only one product spot R$_f$(system II) 0.21 identical, by admixture, to TR-4161. Again, this in vitro experiment demonstrates the ability of an esterase to convert an enol acylate prostaglandin analog into its corresponding E class prostaglandin.

EXAMPLE XXX

Evaluation of the Effects on Human Isolated Bronchial Muscle In Vitro

The procedure described by P. J. Gardiner, et al. (Prostaglandins, 19 (6), 819 (1980)) was used to assess the influence of test compounds on bronchial dilatory or constrictor activity on human bronchial muscle. The method described in Example 43(G) of U.S. Pat. No. 4,220,795 was used to evaluate the effects on the guinea pig trachea. Macroscopically normal human lung tissue was dissected immediately after surgical lobectomy or pneumonectomy for carcinoma of the lung. Tertiary bronchioles (approximately 2–4 mm diameter) were dissected from this tissue and cleaned of connective tissues, blood vessels, etc. The bronchioles were cut spirally, and stored for 12-24 hours in Krebs Henseleit solution at 4° C. On the following day, the spiral preparation was mounted and its movement recorded as with guinea-pig trachea, except that the preparation was allowed to equilibrate for 90 min. before the experiment began. The same paired arrangement of tests was used for experiments on drug interactions, as with the guinea-pig trachea. The activity judgement value was assigned as with the guinea-pig trachea according to the following schedule:

| Response | Value Judgement |
|---|---|
| More relaxation at 0.01 mcg/ml than that elicited by $PGE_1$ | R4 |
| More relaxation at 0.1 mcg/ml than that elicited by $PGE_1$ | R3 |
| More relaxation at 1.0 mcg/ml than that elicited by $PGE_1$ | R2 |
| More relaxation at 10.0 mcg/ml than that elicited by $PGE_1$ | R1 |
| More than 0 but less relaxation at any concentration than that elicited by $PGE_1$ | R0 |
| No effect at any concentration | 0 |
| More than 0 but less contraction at any concentration than the degree of relaxation elicited by $PGE_1$ | C0 |
| More contraction at 10.0 mcg/ml than the degree of relaxation elicited by $PGE_1$ | C1 |
| More contraction at 1.0 mcg/ml than the degree of relaxation elicited by $PGE_1$ | C2 |

The results of the test compounds effects on human bronchial muscle and guinea pig trachea are given in Table 1.

TABLE 1
Effects of Test Compounds on Human Bronchial Muscle and Guinea Pig Trachea.

| Example No. | TR/MLS No. | Human Bronchial Muscle | Guinea Pig Trachea |
|---|---|---|---|
| II | 7099 | R1 | R3 |
| III | 7101 | C | — |
| V | 7110 | C | — |
| V | 7111 | R1 | — |
| VI | 7112 | R1 | — |
| VI | 7113 | C | C |
| VII | 7115 | C | C |
| VIII | 7128 | R2 | C |
| VIII | 7129 | R2 | R2 |
| XXV | 7130 | R4 | R2 |
| XIII | 7132 | R0 | C |
| XIV | 7138 | R1 | R1 |
| X | 7140 | R0 | — |
| XII | 7143 | C | — |
| XVIII | 7154 | R0 | — |
| XVII | 7158 | R3 | — |
| XVIII | 7159 | R1 | — |

EXAMPLE XXXI

Evaluation of the Gastric Antisecretory Effects in Heidenhain Pouch Dogs

Storage and Pharmaceutical Preparation of Compounds Prostanoids were dissolved in ethanol at 20, 50 or 100 mg./ml. in order to provide the minimal amount of alcohol to the animals, and solutions stored at −14° C. Solutions older than two weeks were usually discarded. When the prostanoids were given by the oral route to dogs, a gelatin capsule was filled with methylcellulose and the corresponding amount of the prostaglandin solution being tested dripped into the excipient and the capsule closed. Capsules were prepared individually for each dog just a few minutes before administration. When the prostanoids were administered by the intravenous route, the amount required was taken from a 20 mg./ml. ethanol solution and diluted further with isotonic saline.

Heidenhain Pouch Dogs

Mongrel dogs of both sexes (14-20 kg.) were provided with a Heidenhain pouch and allowed to recover from surgery for at least 40 days. During this time, animals were trained to remain quietly in a Pavlov stand. On the day previous to the experiment, food was withdrawn 18 hours before but water was allowed ad libitum. Dogs were placed in the stand, a peripheral vein cannulated and samples of secretion taken from the pouch every 15 min. throughout the experiment. Basal secretion was nearly zero, but increased when an intravenous infusion of histamine dihydrochloride was applied at a rate of 1 mg./dog/hr. One hour after starting the infusion either the compound being tested or the vehicle was administered and its effect on the secretory response to histamine was assessed during a period of 270 min. The volume of each sample was measured and acidity determined using a 1 ml. aliquot titrated with NaOH (0.1 N) to pH 7.0. Animals were used several times with an interval of at least one week between experiments. Each dog received the vehicle, as well as all the doses tested (unless otherwise stated). The sequence in which animals received the vehicle and the doses of a given compound were different for most dogs.

Table 2 describes the gastric antisecretory effects of the test agents.

TABLE 2
Gastric Antisecretory Effects of Prostaglandin Analogs

| Example No. | TR/MLS No. | Dose p.o. (mg./kg.) | Total Acid Output mEq/270 min. | Volume Secreted ml/270 min. |
|---|---|---|---|---|
| XI | 7141 | 0.16 | 15.89 ± 4.71 | 96.8 ± 11.6 |
| — | control | 0 | 30.18 ± 4.56 | 175.2 ± 25.8 |
| XVII | 7177 | 0.16 | 4.84 ± 2.10 | 32.7 ± 12.6 |
| — | control | 0 | 27.17 ± 7.57 | 161.3 ± 43.3 |

Similarly, MLS-7174 (Example No. XXIII) inhibited gastric secretion in the above protocol at 0.160 mg./kg. and 0.040 mg./kg. (p.o.). At a dose of 0.020 mg./kg. no inhibition of gastric secretion was observed.

EXAMPLE XXXII

Evaluation of MLS-7174 on the Embrotoxicity and Acceleration of Parturition in the Albino Rat Two groups (A and B) of inseminated female albino rats (10 per group) were maintained on food and water ad libitum. MLS-7174 (Example XXIII) was administered as a 4.8% ethanolic solution in 0.15 M phosphate buffer (pH 7.4) at a concentration of 4.8 mg./ml. This solution was stored, when not in use, at 0° to 5° C.

In group A, a single dose of 500 μg/kg. of MLS-7174 was administered via the caudal vein on day 10 of gestation. On day 20 of gestation these 10 females were terminated via cervical dislocation and reproductive efficiency was determined. In group B, three intravenous doses of 500 μg/kg. were administered via the caudal vein on day 18 of gestation. These females were allowed to deliver their offspring. The length of gestation and viability of offspring were noted. An additional group (C) of three females were treated in a similar manner with the exception that they received 3×5 mg./kg. intravenous doses on day 18 of gestation.

Results:

1. Group A. Eight of ten (80%) females were found to be pregnant and all eight had embryonic loss, including one female with only an implantation scar. Although no control females were used for comparison, historical data from a collection of 105 teratology studies indicate less than 7% resorption rate would be expected versus a 15% resorption rate in this group.

2. Group B/C. Eight of 10 (80%) females (Group B) were found pregnant at termination. Five of the eight pregnant females delivered on day 20 of gestation and the three others by the afternoon of day 21. Normal gestation in the rat averages 22-23 days.

Two of the three females in Group C delivered on day 20. Additionally, some females (in both groups) had one or more dead pups following delivery and all but one had post-implantation loss. 3.

The results of these studies demonstrates the potential of MLS-7174 as an abortificant agent and as an agent to effectively accelerate the precipitation of parturition in animals and man.

EXAMPLE XXXIII

Evaluation of Potential and Ionic Fluxes in Heidenhain Pouch dogs—A Measure of Cytoprotectivity The procedure used to evaluate the modification of the gastric transmucosal potential difference and the changes of ionic fluxes induced by aspirin was based on those described by Davenport et al, *Gastroenterology*, 47, 142-152, (1964) and Cooke et al, [ibid, 66, 56-62, (1974)]. Heidenhain pouch dogs were placed in a Pavlov stand, after a fasting period of 18 hrs., and a Thomas Cannula was connected from the pouch to a glass recipient via rubber and tygon tubing. The glass recipient was located approximately 15 cm. higher than the pouch. The transmucosal potential difference was measured by means of two polyethylene tubes filled with 3% agar in saturated KCl. The detecting electrode (PE-90) was introduced in the pouch through the rubber tube and the reference electrode (PE-50) in a peripheral vein. The other end of each electrode was placed in a 50 ml. suction flask containing a Beckman calomel cell. The two calomel cells were connected to a 7P Grass polygraph previously calibrated to record the potential difference. In order to measure the ionic fluxes, the pouch was filled with 33 ml. of distilled water containing 30 mM of HCl and 54 mM of NaCl (solution A) by means of a catheter connected to a syringe. After rinsing the syringe three times, a 3 ml. aliquot was saved for analysis and 30 minutes later the liquid was drained from the pouch, the volume measured, and a sample taken for analysis. The total acid of samples was determined by titration to pH 7.0, and the amounts of Na and K assessed by means of a Beckman (KLiNa) flame photometer. Differences between the initial and the 30 minute sample (multiplied by the corresponding volume) were considered as the net inflow or outflow of $H^{30}$, $Na^+$ or $K^+$ fluxes. These observations were performed in four consecutive 30 minute periods. The values obtained during the first period were quite variable, therefore, this lapse was considered as a stabilization time and the corresponding data were not used. During the second period, the changes of ionic fluxes were more stable and these values were taken as control data. Between the first and the second period, dogs received an intravenous injection of 10 μg/kg. of the test compound or the vehicle. The liquid (solution B) in the third period contained 30 mM of aspirin suspended in solution A. Since aspirin is not soluble at a low pH, solution B was kept on a magnetic stirrer under continuous agitation in order to assure the administration of the desired amount of aspirin. In the fourth period solution A was again administered (recovery period). Table 3 shows the decrement in potential difference induced by aspirin and the antagonism of this effect produced by the previous intravenous administration of 10 μg/kg. of the test compound one half hour before.

It is well known that a high concentration of aspirin (30 mM) at a low pH in contact with the gastric mucosa results in a lesion of this structure [op.cit., Dajani, E.Z., et al., *Am.J.Dig.Dis.*, 23, 436-442 (1978)]. In this study, such lesion was manifested by a decrease in the transmucosal potential difference (Table 4), specifically in the lines of data referring to difference between the third (aspirin) or fourth (recovery) periods with the second (control).

Results

The contact of 30 mM of aspirin with the gastric mucosa resulted in a decrease of the potential difference of 46% (from −68 mV to −37 mV). The finding that the test compound, MLS-7177, was able to inhibit significantly the changes in transmucosal potential difference as well as the $H^+$ and $K^+$ fluxes induced by aspirin, strongly suggests [see Cotton, D.G., et al, *J.Pharmacol.Exp.Ther.*, 210, 253-288 (1979)] that this compound exerts a cytoprotective effect on the gastric mucosa.

TABLE 3

Effect of MLS-7177 on the decrement of transmucosal potential difference induced by aspirin in Heidenhain in pouch dogs.

| Time (min) | CONTROL (2nd period) | | ASPIRIN (30 mM) (3rd period) | | RECOVERY (4th period) | |
|---|---|---|---|---|---|---|
| | Vehicle | MLS-7177[a] | Vehicle | MLS-7177 | Vehicle | MLS-7177 |
| 3 | 67 ± 2 | 68 ± 1[b] | 57 ± 2 | 68 ± 3* | 37 ± 3 | 51 ± 2* |
| 6 | 67 ± 2 | 68 ± 1 | 50 ± 1 | 60 ± 2* | 38 ± 5 | 51 ± 2 |
| 9 | 66 ± 2 | 68 ± 1 | 45 ± 1 | 55 ± 2* | 39 ± 5 | 51 ± 1 |
| 12 | 66 ± 2 | 68 ± 1 | 43 ± 2 | 54 ± 2* | 39 ± 5 | 50 ± 2 |
| 15 | 66 ± 2 | 68 ± 1 | 39 ± 1 | 52 ± 2* | 40 ± 5 | 50 ± 1 |
| 18 | 66 ± 2 | 69 ± 1 | 38 ± 1 | 51 ± 2* | 41 ± 5 | 51 ± 2 |
| 21 | 67 ± 2 | 69 ± 2 | 37 ± 2 | 50 ± 2* | 42 ± 5 | 51 ± 1 |
| 24 | 68 ± 2 | 69 ± 2 | 37 ± 1 | 49 ± 1* | 42 ± 6 | 52 ± 1 |
| 27 | 68 ± 2 | 69 ± 1 | 37 ± 2 | 48 ± 1* | 44 ± 6 | 53 ± 1 |

TABLE 3-continued

Effect of MLS-7177 on the decrement of transmucosal potential difference induced by aspirin in Heidenhain in pouch dogs.

| Time (min) | CONTROL (2nd period) | | ASPIRIN (30 mM) (3rd period) | | RECOVERY (4th period) | |
|---|---|---|---|---|---|---|
| | Vehicle | MLS-7177[a] | Vehicle | MLS-7177 | Vehicle | MLS-7177 |
| 30 | 68 ± 2 | 68 ± 1 | 37 ± 2 | 48 ± 1* | 45 ± 10 | 53 ± 2 |

[a]MLS-7177 was administered at 10 μg/kg, i.v. at the begining of the control period.
[b]Results are expressed as negative mV; data correspond to mean values ± S.E. from three experiments.
*Statistically significantly different from experiments where animals received only the vehicle (p < 0.05 by the t test).

TABLE 4

Influence of MLS-7177 on the Aspirin-induced modifications of ionic fluxes in Heidenhain pouch dogs.[a]

| Period | Vehicle | MLS-7177 |
|---|---|---|
| | $H^+$ Fluxes (μEq/30 min) | |
| 2 | −96 ± 128[a,b] | −80 ± 47 |
| 3 | −437 ± 114 | −312 ± 238 |
| 4 | −512 ± 47 | −129 ± 17* |
| 3-2 | −341 ± 82[c] | −232 ± 208 |
| 4-2 | −350 ± 103[c] | −50 ± 61* |
| | $Na^+$ Fluxes (μEq/30 min) | |
| 2 | 88 ± 35 | 97 ± 41 |
| 3 | 194 ± 51 | 198 ± 51 |
| 4 | 370 ± 97 | 245 ± 94 |
| 3-2 | 106 ± 66 | 101 ± 18 |
| 4-2 | 281 ± 62 | 148 ± 74 |
| | $K^+$ Fluxes (μEq/30 min) | |
| 2 | 6.6 ± 1.2 | 8.8 ± 1.9 |
| 3 | 22.3 ± 3.4 | 13.1 ± 3.1 |
| 4 | 27.1 ± 7.2 | 12.9 ± 4.5 |
| 3-2 | 15.6 ± 2.2 | 4.3 ± 1.3* |
| 4-2 | 20.5 ± 6.1 | 4.0 ± 2.7 |

[a]Positive values indicate that the amount of ions in the pouch content have increased at the end of the 30 min period in relation to the initial sample and negative values, the opposite.
[b]Values represent means ± S.E. from three experiments.
[c]Algebraic differences between values found in the third or fourth and the control period (second).
*Statistically significantly different from data obtained in vehicle treated animals (p < 0.05 by the t test).

What is claimed is:

1. Prostaglandin C-9 enol acylate analogs characterized by the formula:

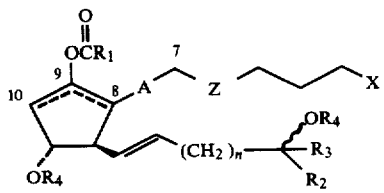

wherein: the dashed line in the cyclopentyl ring represents the presence of a double carbon-carbon bond at either $C_8-C_9$ or $C_9-C_{10}$; Z is cis vinylene or ethylene; n is 0 or 1; A represents the presence of a single carbon-carbon bond between $C_7$ and $C_8$ which is in the α configuration when there is a double carbon-carbon bond between $C_9$ and $C_{10}$ and is in the plane of the 5 membered ring when there is a double carbon-carbon bond between $C_8$ and $C_9$; X is $CH_2OH$, $CH_2OCOCH_3$, $CONHR_4$, $CO_2M$ where M is $H^+$, $K^+$, ½ $Ca^{++}$, $NH_3^+C(C_2H_5OH)_3$ or another pharmacologically acceptable salt cation, $CH_3$ or $C_2H_5$; $R_1$ is n-alkyl of 1 to 20 carbon atoms which is optionally replaced with oxa groups, cyclic alkyl or 3 to 12 carbon atoms optionally replaced with nitrogen to form an imido group of the formula

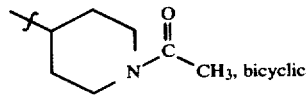

bicyclic alkyl of 7 to 12 carbon atoms, aryl of 6 to 12 carbon atoms optionally substituted with an n-alkyl group of 1 to 10 carbon atoms or one or more halogen atoms, alkenyl (Z and/or E) of 2 to 12 carbon atoms, alkenyl-alkyl of 3 to 12 carbon atoms or O-n-alkyl of 1 to 20 carbon atoms wherein all of the above are optionally substituted with $CO_2M$, $CONHR_4$ or acetate; $R_2$ is H, n-alkyl of 1 to 10 carbon atoms, branched alkyl of 3 to 10 carbon atoms, cyclic alkyl of 3 to 10 carbon atoms optionally substituted with n-alkyl of 1 to 10 carbon atoms, bicyclic alkyl of 7 to 12 carbon atoms, aryl of 6 to 12 carbon atoms optionally substituted with n-alkyl of 1 to 10 carbon atoms or halogen, $R_3$ is a moiety coming within the definition of $R_2$ except that $R_3$ is not H; and $R_4$ is H or a moiety coming within the definition of $COR_1$.

2. A compound as defined by claim 1 wherein the double bond is at $C_8-C_9$, Z is ethylene, n is 0, X is $CH_2OH$, $R_1$ is $CH_3$, $R_4$, $R_2$ are H, $R_3$ is $C_5H_{11}$ and $R_4$ is H with the 15—OH group comprising $OR_4$ being in the β-configuration.

3. A compound as defined by claim 1 wherein the double bond is at $C_8-C_9$, Z is ethylene, n is 1, X is $CH_2OH$, $R_1$ is $CH_3$, $R_2$ is $C_4H_9$, $R_3$ is $CH_3$ and $R_4$ is H, with the 16—OH group comprising $OR_4$ being in either the β or α-configuration.

4. A compound as defined by claim 1 wherein the double bond is at $C_8-C_9$, Z is ethylene, n is 1, X is $CH_2OH$, $R_1$ is $CH_3$, $R_2$ is $C_4H_9$, $R_3$ is $CH_3$, $R_4$ is H with the 16—OH group comprising $OR_4$ being in either the α or β-configuration, and the double bond between $C_{13}-C_{14}$ in the Z configuration.

5. A compound as defined in claim 1 wherein the double bond is at $C_8-C_9$, Z is ethylene, n is 0, X is $CH_2OH$, $R_1$ is i-propyl, $R_2$ is H, $R_3$ is cyclohexyl and $R_4$ is H with the 15—OH group comprising $OR_4$ being in the α-configuration.

6. A compound as defined by claim 1 wherein the double bond is at $C_9-C_{10}$, Z is ethylene, n is 0, X is $CH_2OH$, $R_1$ is $CH_3$, $R_2$ is H, $R_3$ is $C_5H_{11}$ and $R_4$ is H with the 15—OH group comprising $OR_4$ being in the α-configuration.

7. A compound as defined by claim 1 wherein the double bond is at $C_8-C_9$, Z is ethylene, n is 0, X is $CH_2OH$, $R_1$ is $CH_3$, $R_2$ is H, $R_3$ is cyclohexyl and $R_4$ is H with the 15—OH group comprising $OR_4$ being in the α-configuration.

8. A compound as defined by claim 1 wherein the double bond is at $C_8$–$C_9$, Z is ethylene, n is 0, X is $CH_2OH$, $R_1$ is $CH_3$, $R_2$ is H, $R_3$ is $C_5H_{11}$ and $R_4$ is H with the 15—OH group comprising $OR_4$ being in the α-configuration.

9. A compound as defined by claim 1 wherein the double bond is at $C_9$–$C_{10}$, Z is ethylene, n is 1, X is $CH_2OH$, $R_1$ is $CH_3$, $R_2$ is $C_4H_9$, $R_3$ is $CH_3$, and $R_4$ is H with the 15—OH group comprising $OR_4$ being in either the β or α-configuration.

10. A compound as defined by claim 1 wherein $R_1$ is

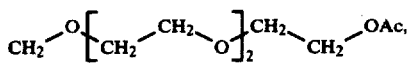

the double bond is at $C_8$–$C_9$, Z is ethylene, n is 0, X is $CH_2OH$, $R_2$ is H, $R_3$ is $C_5H_{11}$ and $R_4$ is H with the 15—OH group comprising $OR_4$ being in the β-configuration.

11. A compound as defined by claim 1 wherein $R_1$ is

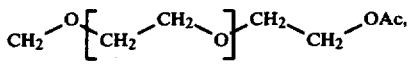

the double bond is at $C_8$–$C_9$, Z is ethylene, n is 0, X is $CH_2OH$, $R_2$ is H, $R_3$ is $C_5H_{11}$ and $R_4$ is H with the 15—OH group comprising $OR_4$ being in the α-configuration.

12. A compound as defined by claim 1 wherein the double bond is at $C_8$–$C_9$, Z is ethylene, n is 0, X is $CH_2OH$, $R_1$ is O-s-butyl, $R_2$ is H, $R_3$ is $C_5H_{11}$ and $R_4$ is H with the 15—OH group comprising $OR_4$ being in the α-configuration.

13. A compound as defined by claim 1 wherein the double bond is at $C_8$–$C_9$, Z is ethylene, n is 0, X is $CH_2OH$, $R_1$ is N-acetyl-4-piperidinyl, $R_2$ is H, $R_3$ is $C_5H_{11}$ and $R_4$ is H with the 15—OH group comprising $OR_4$ being in the α-configuration.

14. A compound as defined by claim 1 wherein the double bond is at $C_8$–$C_9$, Z is ethylene, n is 0, X is $CH_2OH$, $R_1$ is —$(CH_2)_4CO_2H$, $R_2$ is H, $R_3$ is $C_5H_{11}$ and $R_4$ is H with the 15—OH group comprising $OR_4$ being in the α-configuration.

15. A compound as defined by claim 1 wherein the double bond is at $C_8$–$C_9$, Z is ethylene, n is 0, X is $CH_2OH$, $R_1$ is —$(CH_2)_2CO_2H$, $R_2$ is H, $R_3$ is $C_5H_{11}$ and $R_4$ is H with the 15—OH group comprising $OR_4$ being in the α-configuration.

16. A compound as defined by claim 1 wherein the double bond is at $C_8$–$C_9$, Z is ethylene, n is 0, X is $CH_2OH$, $R_1$ is —$(CH_2)_2$—$CO_2CH_3$, $R_2$ is H, $R_3$ is $C_5H_{11}$ and $R_4$ is H with the 15—OH group comprising $OR_4$ being in the α-configuration.

17. A compound as defined by claim 1 wherein the double bond is at $C_8$–$C_9$, Z is ethylene, n is 1, X is $CH_2OAc$, $R_1$ is $CH_3$, $R_2$ is $C_4H_9$, $R_3$ is $CH_3$ and $R_4$ is H with the 16—OH group comprising $OR_4$ being in either the β or α-configuration.

18. A compound as defined by claim 1 wherein the double bond is at $C_8$–$C_9$, Z is ethylene, n is 0, X is $CH_2OAc$, $R_1$ is —$(CH_2)_2CO_2H$, $R_2$ is H, $R_3$ is $C_5H_{11}$ and $R_4$ is H with the 15—OH group comprising $OR_4$ being in the α-configuration.

19. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is $C_5H_{11}$ and $R_4$ is acetyl in the 15-position and H in the 11-position with the 15—OAc group comprising $OR_4$ being in the β-configuration.

20. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is $C_5H_{11}$ and $R_4$ is acetyl in the 15-position and H in the 11-position with the 15—OAc group comprising $OR_4$ being in the α-configuration.

21. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is cyclohexyl and $R_4$ is H with the 15—OH group comprising $OR_4$ being in the α-configuration.

22. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is $C_5H_{11}$ and $R_4$ is acetyl at the 11 and 15-positions with the 15—OAc group comprising $OR_4$ being in the α-configuration.

23. A compound as defined by claim 1 wherein the double bond is at $C_8$–$C_9$, Z is cis vinylene, n is 0, X is $CO_2C_2H_5$, $R_1$ is $CH_3$, $R_2$ is H, $R_3$ is $C(CH_3)_2C_4H_9$ and $R_4$ is H with the 15—OH group comprising $OR_4$ being in the α-configuration.

24. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is

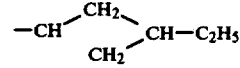

and $R_4$ is H with the 15—OH group comprising $OR_4$ being in the β-configuration.

25. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is

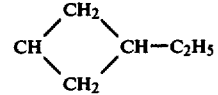

and $R_4$ is H with the 15—OH group comprising $OR_4$ being in the α-configuration.

26. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is $CH(CH_3)C_4H_9$-n and $R_4$ is H with the 15—OH group comprising $OR_4$ being in the β-configuration.

27. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is $C(CH_3)_2$—$C_4H_9$-n and $R_4$ is H with the 15—OH group comprising $OR_4$ being in the β-configuration.

28. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is $C(CH_3)_2C_4H_9$—n and $R_4$ is H with the 15—OH group comprising $OR_4$ being in the α-configuration.

29. A compound as defined by claim 1 wherein the double bond is at $C_8$–$C_9$, Z is cis-vinylene, n is 0, X is $CO_2C_2H_5$, $R_1$ is $CH_3$, $R_2$ is H, $R_3$ is -$C(CH_3)_2C_4H_9$-n and $R_4$ is H with the 15—OH group being in the $\beta$-configuration.

30. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is $CH(CH_3)C_4H_9$-n and $R_4$ is H with the 15—OH group being in the $\alpha$-configuration.

31. A compound as defined by claim 1 wherein the double bond is at $C_8$–$C_9$, Z is cis-vinylene, n is 0, X is $CO_2C_2H_5$, $R_1$ is $CH_3$, $R_2$ is H, $R_3$ is $C_5H_{11}$ and $R_4$ is H with the 15—OH group being in the $\alpha$-configuration.

32. A compound as defined by claim 1 wherein the double bond is at $C_8$–$C_9$, Z is ethylene, n is 0, X is $CO_2CH_3$, $R_1$ is $CH_3$, $R_2$ is H, $R_3$ is $C_5H_{11}$ and $R_4$ is H with the 15—OH group comprising $R_4$ being in the $\alpha$-configuration.

33. A compound as defined in claim 1 wherein the double bond is at $C_8$–$C_9$, Z is ethylene, n is 0, X is $CO_2H$, $R_1$ is $CH_3$, $R_2$ is H, $R_3$ is $C_5H_{11}$ and $R_4$ is H with the 15—OH group comprising $OR_4$ being in the $\alpha$-configuration.

34. A compound as defined by claim 1 wherein the double bond is at $C_8$–$C_9$, Z is cis-vinylene, n is 0, X is $CO_2H$, $R_1$ is $CH_3$, $R_2$ is H, $R_3$ is $C(CH_3)_2C_4H_9$ and $R_4$ is H with the 15—OH group comprising $OR_4$ being in the $\beta$-configuration.

35. A compound as defined by claim 1 wherein the double bond is at $C_8C_9$, Z is cis-vinylene, n is 0, X is $CO_2H$, $R_1$ is $CH_3$, $R_2$ is H, $R_3$ is $C(CH_3)_2C_4H_9$ and $R_4$ is H with the 15—OH group comprising $OR_4$ being in the $\alpha$-configuration.

36. A compound as defined by claim 1 wherein the double bond is at $C_8$–$C_9$, Z is ethylene, n is 1, X is $CO_2CH_3$, $R_1$ is $CH_3$, $R_2$ is H, $R_3$ is $C(CH_3)_2C_3H_7$ and $R_4$ is H with the 16—OH group comprising $OR_4$ being in the $\alpha$-configuration.

37. A compound as defined by claim 1 wherein the double bond is at $C_8$–$C_9$, Z is ethylene, n is 1, X is $CO_2CH_3$, $R_1$ is $CH_3$, $R_2$ is H, $R_3$ is $C(CH_3)_2C_3H_7$ and $R_4$ is H with the 16—OH group comprising $OR_4$ being in the $\beta$-configuration.

38. A method of inhibiting the formation of lesions in the gastrointestinal tract of an individual which method involves introducing to the gastro-intestinal tract of such individual a lesion inhibiting (cytoprotective) amount of 9-acetoxy-16-methyl-1, 11$\alpha$,16RS-trihydroxy-prosta-9,13E-diene.

* * * * *